United States Patent
Wessels et al.

(10) Patent No.: US 10,722,466 B2
(45) Date of Patent: Jul. 28, 2020

(54) LIPOSOMAL FORMULATION FOR USE IN THE TREATMENT OF CANCER

(71) Applicants: LES LABORATOIRES SERVIER, Suresnes (FR); NOVARTIS AG, Basel (CH)

(72) Inventors: Peter Wessels, Basel (CH); Henricus Tiemessen, Basel (CH); Paolo De Marco, Basel (CH); Malika Larabi, Basel (CH); Christiane Schiedel, Basel (CH); Marina Gurina, Basel (CH)

(73) Assignees: LES LABORATOIRES SERVIER, Suresnes (FR); NOVARTIS AG, Basel (CH)

( * ) Notice: Subject to any disclaimer, the term of this patent is extended or adjusted under 35 U.S.C. 154(b) by 0 days.

(21) Appl. No.: 16/344,431

(22) PCT Filed: Oct. 27, 2017

(86) PCT No.: PCT/EP2017/077538
§ 371 (c)(1),
(2) Date: Apr. 24, 2019

(87) PCT Pub. No.: WO2018/078064
PCT Pub. Date: May 3, 2018

(65) Prior Publication Data
US 2020/0054557 A1 Feb. 20, 2020

(30) Foreign Application Priority Data
Oct. 28, 2016 (EP) .................................. 16306415

(51) Int. Cl.
| A61K 9/127 | (2006.01) |
| A61K 9/107 | (2006.01) |
| A61K 31/519 | (2006.01) |
| A61K 47/02 | (2006.01) |
| A61K 47/10 | (2017.01) |
| A61K 47/24 | (2006.01) |
| A61K 47/26 | (2006.01) |
| A61K 9/00 | (2006.01) |
| A61K 9/08 | (2006.01) |

(52) U.S. Cl.
CPC .......... A61K 9/1271 (2013.01); A61K 9/1075 (2013.01); A61K 31/519 (2013.01); A61K 47/02 (2013.01); A61K 47/10 (2013.01); A61K 47/24 (2013.01); A61K 47/26 (2013.01); *A61K 9/0019* (2013.01); *A61K 9/08* (2013.01)

(58) Field of Classification Search
None
See application file for complete search history.

(56) References Cited

U.S. PATENT DOCUMENTS 6,239,102 B1 5/2001 Tiemessen
2008/0131499 A1 6/2008 Leigh et al.

FOREIGN PATENT DOCUMENTS

| CN | 103622911 | 3/2014 |
| EP | 1389089 | 8/2009 |
| WO | WO 87/07502 | 12/1987 |
| WO | WO 02/080883 | 10/2002 |
| WO | WO 2008/114274 | 9/2008 |
| WO | WO 2010/036947 | 4/2010 |
| WO | WO2015/097123 | 7/2015 |

OTHER PUBLICATIONS

Habib Ali et al., International Journal of Pharmaceutics, 2013, 453, 225-232.
Meidan et al., J Liposome Res., 2006, 16, 27-43.
Mu et al., International Journal of Pharmaceutics, 2013, 453, 215-224.
Salonen et al., Biochimica et Biophysica Acta, 1989, 982, 205-215.
SUPRAVAIL® Fact Sheet, Phares, 2006.
Van Hoogevest et al., PDA J. Pharm. Science and Techn., 2006, 60, 366-377.
Yinchoncharoan et al., Pharmacological Reviews, 2016, 68, 701-787.
International Search Report for PCT/EP2017/077538 dated Nov. 29, 2017.
Li, Jing, et al., "A review on phospholipids and their main applications in drug delivery systems", Asian Journal of Pharmacutical Sciences, 10, 2015, pp. 81-98.
Shabbits, Jennifer, A., et al., "Development of an in vitro drug release assay that accurately predicts in vivo drug retention for liposome-based delivery systems", Journal of Controlled Release, 84, 2002, pp. 161-170.

*Primary Examiner* — Brian J Davis
(74) *Attorney, Agent, or Firm* — Hueschen and Sage

(57) ABSTRACT

The invention relates to a pharmaceutical liposomal composition comprising 2-{[5-{3-chloro-2-methyl-4-[2-(4-methylpiperazin-1-yl)ethoxy]phenyl}-6-(4-fluorophenyl) thieno [2,3-d]pyrimidin-4-yl]oxy}-3-(2-{[2-(2-methoxyphenyl)pyrimidin-4-yl]methoxy}phenyl) propanoic acid, referred to herein as 'Compound A', or a pharmaceutically acceptable salt thereof. More specifically the invention relates to a liposomal vehicle, an organic concentrate composition comprising Compound A, and a pharmaceutical composition for parenteral administration comprising liposomes and Compound A. Furthermore, the invention relates to the use of such compositions for the treatment of cancer. 'Compound A' as used herein includes all enantiomers, diastereoisomers, and atropisomers thereof, or mixtures thereof, and also optionally includes the pharmaceutically acceptable salts thereof.

42 Claims, 4 Drawing Sheets

Efficacy and tolerability of liposomal formulated Compound A after 10 mg/kg QW administration in female nude rats bearing MV4;11 AML xenografts

\* $p < 0.05$, compared with vehicle group (one way ANOVA with post hoc Dunnett's test).

Efficacy and tolerability of liposomal formulated Compound A after 30 mg/kg QW administration in female nude rats bearing MV4;11 AML xenografts

* $p < 0.05$, compared with vehicle group (one way ANOVA with post hoc Dunnett's test).

FIGURE 4

Release profile of Compound A from SUV to 100 % ePC MLV at different SUV:MLV (v/v) ratios

LIPOSOMAL FORMULATION FOR USE IN THE TREATMENT OF CANCER

BACKGROUND OF THE INVENTION

The invention relates to a pharmaceutical liposomal composition comprising 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, referred to herein as 'Compound A', or a pharmaceutically acceptable salt thereof. More specifically the invention relates to a liposomal vehicle, an organic concentrate composition comprising Compound A, and a pharmaceutical composition for parenteral administration comprising liposomes and Compound A. Furthermore, the invention relates to the use of such compositions for the treatment of cancer. 'Compound A' as used herein includes all enantiomers, diastereoisomers, and atropisomers thereof, or mixtures thereof, and also optionally includes the pharmaceutically acceptable salts thereof.

The structure of Compound A is

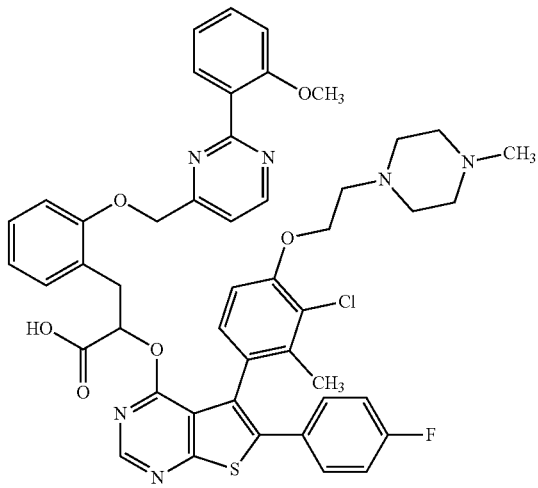 [SMILES: COc1ccccc1-c1nccc(COc2ccccc2CC(Oc2ncnc3sc(-c4ccc(F)cc4)c(-c4ccc(OCCN5CCN(C)CC5)c(Cl)c4C)c23)C(=O)O)n1]

2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

In a particular embodiment, Compound A is:

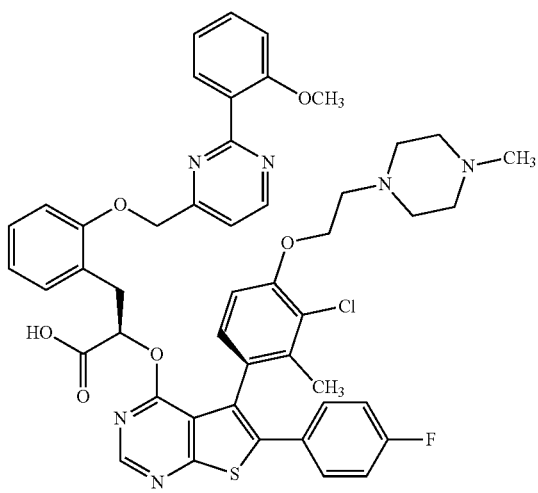

(2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid. In a further embodiment, Compound A used in the composition described herein is the free molecule (not a salt thereof).

The preparation of Compound A, its use as a Mcl-1 inhibitor for the treatment of cancer and pharmaceutical formulations thereof, are described in WO 2015/097123, the content of which is incorporated by reference. The preparation is specifically disclosed in Example 30 of WO 2015/097123.

Compound A is optically active, having one chiral center and chiral axis. It has limited aqueous solubility across all pHs, including physiologically relevant pHs. In order to enable safe and effective administration of Compound A, and to elicit the required therapeutic effects, Compound A needs to be solubilized.

There are different ways to solubilize poorly soluble compounds for parenteral administration. Typical approaches are the optimization of the pH or the use of co-solvents (e.g. PEG300, PEG400, propylene glycol, or ethanol). If these approaches are, for any reason, not feasible, the use of surfactants may be considered (e.g. Tween® 80 or Cremophor EL®). However, these types of surfactants are frequently associated with adverse effects. Cyclodextrins are established as safe solubilizing agents, yet with limitations as they are not effective solubilizers for all compounds. Moreover, compounds with a high solubility in natural oils (e.g. Propofol) may be solubilized in parenteral fat emulsions.

Another possibility to solubilize poorly soluble compounds is the use of phospholipids (van Hoogevest P., Xiangli L., and Alfred F. "Drug delivery strategies for poorly water-soluble drugs: the industrial perspective" *Expert Opinion on Drug Delivery* 2011, 8(11), 1481-1500). Thus, phospholipids present themselves as one additional tool for solubilizing poorly soluble compound besides the usual approaches. However, the solubilization of a certain poorly soluble compound by phospholipids cannot be predicted.

The aim of the current invention is to provide a composition which can conveniently be used to solubilize and parenterally deliver Compound A. In particular, there is a need to provide a pharmaceutical composition for Compound A which is safe and efficacious. Further aims are to provide a composition which is stable in the relevant conditions and containers, and which enables administration of an appropriate dose of Compound A over a reasonable timescale. In a further aim, the composition should be able to be manufactured by a reliable and robust process.

SUMMARY

The present invention provides a composition comprising Compound A, suitable for parenteral administration to patients. In particular, such administration is by intravenous injection or infusion. The invention further provides two separate compositions which can be mixed together shortly before administration to the patient, in order to provide the composition suitable for administration. One composition for mixing is the organic concentrate composition comprising Compound A, and the second composition for mixing is a liposomal vehicle. When the two separate compositions are mixed together, Compound A is loaded into the liposomes within the liposomal vehicle, enabling solubilization of Compound A, and resulting in a pharmaceutical liposomal composition suitable for use in the clinic.

Preferably, the invention provides a composition comprising Compound A, which maintains the chemical stability of Compound A. For example, the formation of the undesired atropisomer and/or oxidation products and/or degradation products, is limited.

Preferably, the invention provides a composition comprising Compound A which has optimal physical stability, for example the formulation of a gel is avoided, and/or the precipitation of components is avoided. It has unexpectedly been found that compositions comprising Compound A are prone to jellification, whereby the composition forms a gel. Such jellification may or may not be reversible. Jellification complicates or prevents the manipulation of the composition comprising Compound A for its proposed use, and needs to be avoided.

The composition (organic concentrate) comprising Compound A should enable efficient and optimal loading of Compound A into liposomes in a liposomal vehicle, by simply mixing the 2 compositions together, shortly before administration to the patient.

Preferably, the invention provides a pharmaceutical liposomal composition which enables a fast release of Compound A from the liposomes after intravenous administration.

Overall, the invention described herein enables effective administration of Compound A to patients, despite the challenging chemical characteristics of Compound A, and challenging physical characteristics of formulations comprising Compound A.

BRIEF DESCRIPTION OF THE FIGURES

FIG. 4 shows the release profile of Compound A from SUV to 100% ePL (egg phospholipids) at various different SUV:MLV ratios (v/v).

DETAILED DESCRIPTION OF THE INVENTION

Figure 1:
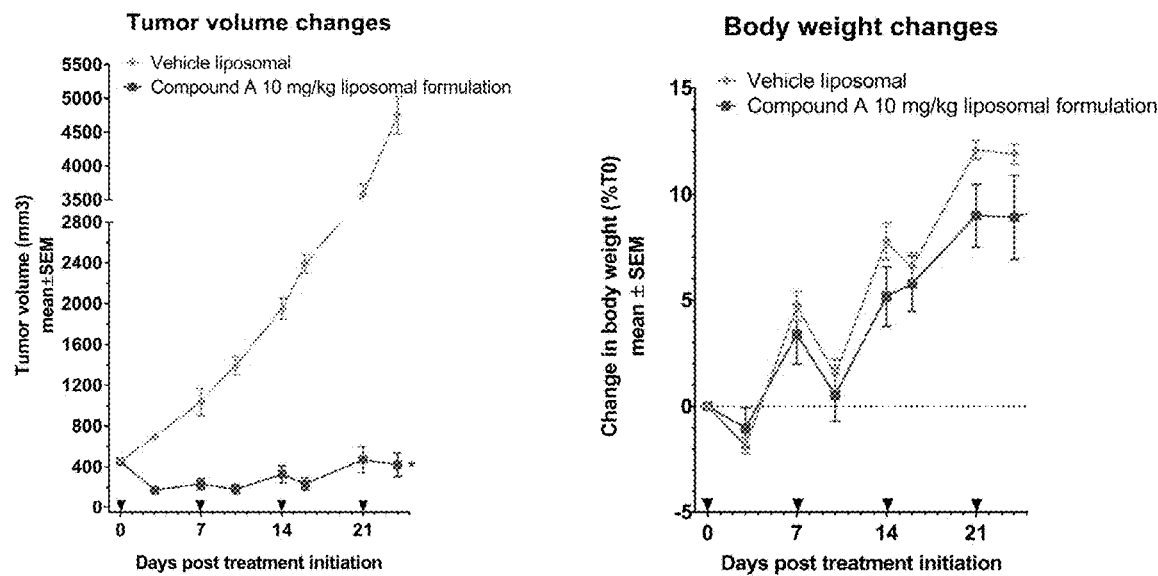
FIG. 1 shows the efficacy and tolerability of liposomal formulated Compound A after 10 mg/kg QW administration in female nude rats bearing MV4;11 AML xenografts.

A liposome is a spherical vesicle having at least one lipid bilayer. The liposome can be used as a vehicle for administration of nutrients and pharmaceutical drugs. Liposomes are most often composed of phospholipids, especially phosphatidylcholine, but may also include other lipids, such as egg phosphatidylethanolamine, so long as they are compatible with lipid bilayer structure.

'liposomal vehicle' as used herein means a liquid comprising liposomes, said liposomes comprising phospholipids. Said liposomal vehicle is suitable for solubilizing Compound A in an aqueous environment after mixing with Compound A, in particular when Compound A is provided as the organic concentrate described herein. Said liposomal vehicle is suitable for loading with Compound A, prior to administration to a patient.

Liposomal size as disclosed herein refers to the size as determined by photon correlation spectroscopy (PCS). The average size expressed as Z average diameter and the polydispersity index are determined using photon correlation spectroscopy according ISO 13321.

The pharmaceutical composition described herein is, in particular, a pharmaceutical liposomal composition. A 'pharmaceutical liposomal composition' means a composition comprising liposomes which is suitable for pharmaceutical administration.

'Jellification' as used herein, means the formation of a gel. On formation of a gel, the composition becomes more viscous, less free-flowing. This makes the composition more difficult, or impossible, to work with for its intended purpose.

The phospholipid used in the liposomal vehicle herein comprises at least one phospholipid of the formula

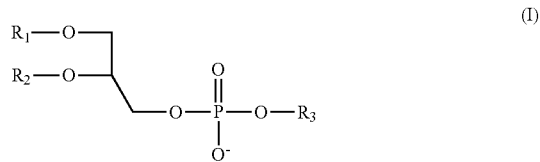

wherein
R$_1$ represents C$_{10}$-C$_{24}$acyl;
R$_2$ represents C$_{10}$-C$_{24}$acyl, or alternatively R$_2$ represents hydrogen or C$_{10}$-C$_{20}$acyl;
R$_3$ represents hydrogen, 2-trimethylamino-1-ethyl, 2-amino-1-ethyl, C$_1$-C$_4$alkyl, C$_1$-C$_5$alkyl substituted by carboxy, C$_2$-C$_5$alkyl substituted by carboxy and hydroxy, C$_2$-C$_5$alkyl substituted by carboxy and amino, an inositol group or a glyceryl group;
or a salt of such compound.

The term acyl used hereinbefore represents the following group:

wherein * is the point of attachment of R$_1$ or R$_2$ to the rest of the molecule, and for example, R is an unbranched alkyl chain, which may be saturated or partially unsaturated.

The phospholipid may be neutral or it may be charged. It may be a double chain or a single chain amphipath. Examples of neutral phospholipids with double chains are phosphatidylcholine (PC), phosphatidylethanolamine (PE) and sphingomyelin. Examples of charged phospholipids are phosphatidic acid (PA), phosphatidyl inositol (PI), and phosphatidylserine (PS) and phosphatidylglycerol (PG). The hydrocarbon chain can either be unsaturated or saturated. In one embodiment, it has from 14 to 18 carbon atoms.

For parenteral formulations, the phospholipid may be a double chain and may contain a fraction of less than 20% of a single chain amphipath. For parenteral formulations, the phospholipid may be phosphatidylcholine (PC) and may contain a fraction of less than 40% of a charged phospholipid.

The single chain lipid is the monoacyl derivative of a neutral or charged phospholipid, but it can also be the monoacyl derivative(s) of glycolipids and sphingolipids. For parenteral use however, the monoacyl derivative is not preferred. Deacylation may be carried out by phospholipase A2 enzyme hydrolysis or by chemical means. The hydrocarbon chain can either be unsaturated or saturated and can have in particular from 14 to 18, or 14 to 24 carbon atoms. The lipids may be derived from natural plant, or animal or microbiological sources, synthesized or partially synthesized, including polyethyleneglycol (PEG) derived monoacyl phospholipids, eg. pegylated monoacyl phosphatidyl ethanolamine.

In a preferred embodiment, $R_2$ is not hydrogen.

In particular, the phospholipid used in the liposomal vehicle described herein is selected from egg lecithin, soy lecithin, or synthetic phospholipids. Examples of synthetic phospholipids for use herein are POPC (palmitoyl oleoyl phosphatidylcholine), DOPC (1,2-Dioleoyl-sn-glycero-3-phosphocholine), DMPC (1,2-Dimyristoyl-sn-glycero-3-phosphocholine) and DPPC (1,2-Dipalmitoyl-sn-glycero-3-phosphocholine), especially the synthetic phospholipids POPC (palmitoyl oleoyl phosphatidylcholine), DOPC (1,2-Dioleoyl-sn-glycero-3-phosphocholine), and DMPC (1,2-Dimyristoyl-sn-glycero-3-phosphocholine), in particular POPC. More particularly, the phospholipid used in the liposomal vehicle is selected from egg lecithin or soy lecithin comprising at least 75% phosphatidylcholine, or at least 70% phosphatidylcholine. In another embodiment, egg lecithin with 71.5% w/w (±7.5% w/w) egg PC (phosphatidylcholine) and 15% w/w (±3% w/w) egg PE (phosphatidylethanolamine) can be used. In a particular embodiment, said phospholipid is selected from Lipoid E 80 S and Lipoid E 80. In a preferred embodiment, said phospholipid is Lipoid E 80 S. Where Lipoid E 80 is used, sodium oleate may optionally be included in the formulation as stabilizer of the colloidal stability.

In preferred embodiments, phospholipids are selected to promote a faster release of Compound A into the bloodstream.

'organic concentrate' as used herein means a composition which is a solution comprising organic, water miscible solvents comprising Compound A, which is suitable for mixing with a liposomal vehicle to enable loading of the liposomes. In particular, said organic concentrate is suitable for mixing with and loading the liposomal vehicle as described herein. The resulting mixture is suitable for administration to a patient.

'Loading' means incorporating or transferring Compound A into liposomes from the organic concentrate.

'negatively charged or polar phospholipid stabiliser' means a phospholipid comprising at least some negatively charged lipids or polar lipid. In particular, the negatively charged or polar phospholipid stabiliser is selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, Lipoid S 75, Lipoid E 80 S, and sodium oleate. In particular, the negatively charged or polar phospholipid stabiliser is 1,2-Dimyristoyl-sn-glycero-3-phospho-rac-glycerol, sodium or ammonium salt, or Lipoid E 80 S, preferably 1,2-Dimyristoyl-sn-glycero-3-phospho-rac-glycerol, sodium salt. Said 'negatively charged or polar phospholipid stabiliser' facilitates the loading of Compound A into liposomes.

The 'negatively charged or polar phospholipid stabiliser' can also be egg lecithin or soy lecithin.

'tonicity adjusting agent' means a pharmaceutically acceptable compound which can be added to a formulation to make it isotonic with human plasma. Tonicity adjusting agents include for example dextrose, glucose, mannitol, sucrose, lactose, trehalose, glycerine and NaCl, in particular sucrose or glycerine, more particularly sucrose. Tonicity is the 'effective osmolality' and is equal to the sum of the concentrations of the solutes which have the capacity to exert an osmotic force across the membrane. Parenteral formulations should be isotonic with blood plasma. Tonicity adjusting agents are well known to the skilled person.

Appropriate solvents can be selected by the skilled formulator. In the organic concentrate herein, the solvent or solvents can be selected from propylene glycol, ethanol, PEG300, Super-Refined® PEG300, PEG400, and Super-Refined® PEG400, in particular propylene glycol and ethanol.

Super-Refined® refers to a high purity grades of PEG300 or PEG400.

A 'buffer' is used to prevent changes in the pH of a solution, and suitable examples are well-known to the skilled formulator.

'Container' means an ampoule or vial with rubber stopper and cap, single or double chamber syringe, infusion bag or bottle made from polymeric materials or glass, suitable for housing compositions for parenteral administration. It also includes any vessel for holding liquids.

'free molecule' as used herein, means the compound is not used in the form of a salt, formed by external counter ions. Compound A may be present in a zwitterionic form, and the term 'free molecule' as used herein includes the zwitterionic form.

As used herein, the term 'comprising' means 'including', and is not intended to exclude the presence of any additional component, unless the context suggests otherwise, for example when the components together sum to 100%.

As used herein, the term 'treat', 'treating' or 'treatment' of any disease or disorder refers in one embodiment, to ameliorating the disease or disorder (i.e., slowing or arresting or reducing the development of the disease or at least one of the clinical symptoms thereof). In another embodiment, 'treat', 'treating' or 'treatment' refers to alleviating or ameliorating at least one physical parameter including those which may not be discernible by the patient. In yet another embodiment, 'treat', 'treating' or 'treatment' refers to modulating the disease or disorder, either physically, (e.g., stabilization of a discernible symptom), physiologically, (e.g., stabilization of a physical parameter), or both.

'Stabiliser against jellification' as used herein, means a stabiliser against jellification of a composition comprising Compound A. This definition of stabiliser includes, for example, electrolytes or polymers. Examples of suitable electrolytes are sodium chloride, potassium chloride, sodium phosphate di- and monobasic, ammonium sulphate and arginine, preferably sodium chloride. Water may be added to the formulation as necessary, with the electrolyte. Examples of suitable polymers are PEG300 and PEG400, in particular PEG300. Stability against jellification can be examined by techniques well known to the skilled person, and in particular, the techniques described herein can be used. Example 12 herein provides techniques which may be employed to test for jellification. When the propensity for jellification of a selected composition is understood, the skilled formulator can use the information to select optimal storage conditions for compositions comprising Compound A.

In one optional embodiment, the PEG300 is Super-Refined® PEG300, which is a high purity PEG300.

In one preferred embodiment, a stabiliser is selected which prevents jellification of the composition comprising Compound A, and which also reduces or prevents precipitation of the components of the composition comprising Compound A. For example, PEG300 is of particular interest in this regard. In one optional embodiment, the PEG300 is Super-Refined® PEG300, and which may also help maintain the chemical stability of Compound A.

Mixing 'shortly before administration to patient' means up to three days before, in particular up to 24 hours before, and for example up to 6 hours before administration to the patient.

'Histidine' as used herein means, in particular, 'L-histidine'.

Advantageously, in certain embodiments of the invention, due to the very small particle size of the liposomes the formulation appears transparent, allowing a visual check of the completeness of the solubilization of Compound A before administration. In a particular embodiment, the composition is intravenously administered to patients.

EMBODIMENTS

Described below are a number of embodiments of the invention.

E1. An organic concentrate composition comprising Compound A which is 2-{[5-{3-chloro-2-methyl-4-[2-(4-methylpiperazin-1-yl)ethoxy]phenyl}-6-(4-fluorophenyl) thieno [2,3-d]pyrimidin-4-yl]oxy}-3-(2-{[2-(2-methoxyphenyl)pyrimidin-4-yl]methoxy}phenyl) propanoic acid, or a pharmaceutically acceptable salt thereof, and a negatively charged or polar phospholipid stabiliser.

E2. An organic concentrate composition according to embodiment E1, comprising Compound A which is (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof, and a negatively charged or polar phospholipid stabiliser.

E3. An organic concentrate composition according to embodiments E1 or E2, wherein Compound A is the free molecule.

E4. An organic concentrate composition according to any of embodiments E1 to E3, wherein the negatively charged or polar phospholipid stabiliser is selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, Lipoid E 80 S, and sodium oleate.

E5. An organic concentrate composition according to any of embodiments E1 to E4, wherein the negatively charged or polar phospholipid stabiliser is dimyristoyl phosphatidylglycerol (DMPG) sodium salt, or Lipoid E 80 S.

E6. An organic concentrate composition according to embodiment E5, wherein the negatively charged or polar phospholipid stabiliser is 1,2-Dimyristoyl-sn-glycero-3-phospho-rac-glycerol, sodium salt.

E7. An organic concentrate composition according to any of embodiments E1 to E6, further comprising one or more solvents.

E8. An organic concentrate composition according to any of embodiments E1 to E7, comprising at least one solvent selected from propylene glycol, ethanol, PEG300 and PEG400.

E9. An organic concentrate composition according to any of embodiments E1 to E8, comprising at least one solvent selected from:
propylene glycol and ethanol, or
propylene glycol, PEG300 and ethanol.

E10. An organic concentrate composition according to any of embodiments E1 to E9, comprising both propylene glycol and ethanol.

E11. An organic concentrate composition according to any of embodiments E1 to E10, further comprising a stabiliser selected from sodium chloride, potassium chloride, sodium phosphate di- and monobasic, ammonium sulphate and arginine, preferably sodium chloride.

E12. An organic concentrate composition according to any of embodiments E1 to E11, further comprising water.

E13. A liposomal vehicle comprising a phospholipid and a tonicity adjusting agent.

E14. A liposomal vehicle according to embodiment E13, comprising from 5% w/w to 20% w/w phospholipid, in particular from 7% w/w to 13% w/w phospholipid.

E15. A liposomal vehicle according to embodiments E13 or E14, wherein the phospholipid is selected from:

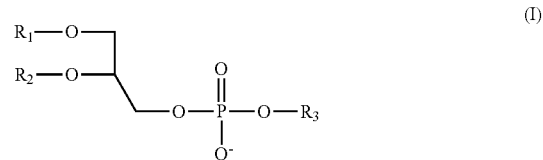

wherein
$R_1$ represents $C_{10}$-$C_{24}$acyl;
$R_2$ represents $C_{10}$-$C_{24}$acyl, or alternatively $R_2$ represents hydrogen or $C_{10}$-$C_{20}$acyl;
$R_3$ represents hydrogen, 2-trimethylamino-1-ethyl, 2-amino-1-ethyl, $C_1$-$C_4$alkyl, $C_1$-$C_5$alkyl substituted by carboxy, $C_2$-$C_5$alkyl substituted by carboxy and hydroxy, $C_2$-$C_5$alkyl substituted by carboxy and amino, an inositol group or a glyceryl group;
or a salt of such compound.

E16. A liposomal vehicle according to embodiments E13 or E14, wherein the phospholipid is selected from egg lecithin, soy lecithin, or synthetic phospholipids.

E17. A liposomal vehicle according to any of embodiments E13 to E16, wherein the phospholipid is selected from egg lecithin, soy lecithin, POPC (palmitoyl oleoyl phosphatidylcholine), DOPC (1,2-Dioleoyl-sn-glycero-3-phosphocholine), and DMPC (1,2-Dimyristoyl-sn-glycero-3-phosphocholine), especially POPC (palmitoyl oleoyl phosphatidylcholine), DOPC (1,2-Dioleoyl-sn-glycero-3- phosphocholine), and DMPC (1,2-Dimyristoyl-sn-glycero-3-phosphocholine), in particular POPC.

E18. A liposomal vehicle according to any of embodiments E13, E14, E16 or E17, wherein the phospholipid is selected from egg lecithin or soy lecithin comprising at least 75% phosphatidylcholine, or at least 70% phosphatidylcholine.

E19. A liposomal vehicle according to any of embodiments E13, E14, E16, E17 or E18, wherein the phospholipid is Lipoid E 80 S.

E20. A liposomal vehicle according to any of embodiments E13 to E19, wherein the tonicity adjusting agent is selected from dextrose, glucose, mannitol, sucrose, lactose, trehalose, glycerine and NaCl.

E21. A liposomal vehicle according to embodiment E20, wherein the tonicity adjusting agent is sucrose or glycerine, in particular sucrose.

E22. A liposomal vehicle according to any of embodiments E13 to E21, further comprising a buffer.

E23. A liposomal vehicle according to embodiment E22, wherein the buffer is histidine.

E24. A liposomal vehicle according to any of embodiments E13 to E23, further comprising water.

E25. A liposomal vehicle according to any of embodiments E13 to E24, wherein the liposomes present in the liposomal vehicle have an average size of from 20 nm to 300 nm, preferably from 20 nm to 100 nm.

E26. A liposomal vehicle according to embodiment E25, wherein the liposomes have an average size of from 20 nm to 80 nm, preferably from 40 nm to 70 nm.

E27. A pharmaceutical composition comprising a phospholipid and Compound A which is 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid, or a pharmaceutically acceptable salt thereof.

E28. A pharmaceutical liposomal composition comprising:
a. a phospholipid as described in any of embodiments E15 to E19, and
b. Compound A which is 2-{[5-{3-chloro-2-methyl-4-[2-(4-methylpiperazin-1-yl) ethoxy]phenyl}-6-(4-fluorophenyl) thieno[2,3-d]pyrimidin-4-yl]oxy}-3-(2-{[2-(2-methoxyphenyl)pyrimidin-4-yl]methoxy}phenyl) propanoic acid, or a pharmaceutically acceptable salt thereof.

E29. The pharmaceutical composition according to embodiment E27, wherein Compound A is (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl] methoxy}phenyl)propanoic acid or a salt thereof, preferably the free molecule.

E30. The pharmaceutical liposomal composition according to embodiment E28, wherein Compound A is (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl] methoxy}phenyl) propanoic acid or a salt thereof, preferably the free molecule.

E31. The pharmaceutical composition according to any of embodiments E27 to E30, for infusion or intravenous injection.

E32. The pharmaceutical composition according to any of embodiments E27 to E31, comprising from 5% w/w to 20% w/w phospholipid, in particular from 7% w/w to 13% w/w phospholipid.

E33. The pharmaceutical composition according to any of embodiments E27 to E32, wherein the phospholipid is selected from those described in embodiments E15 to E19, in particular E18 or E19.

E34. The pharmaceutical composition according to any of embodiments E27 to E33, further comprising a negatively charged or polar phospholipid stabiliser.

E35. The pharmaceutical composition according to embodiment E34, wherein the negatively charged or polar phospholipid stabiliser is selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)])
sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, Lipoid E 80 S, and sodium oleate, in particular dimyristoyl phosphatidylglycerol (DMPG) sodium salt, 1,2-Dimyristoyl-sn-glycero-3-phospho-rac-glycerol sodium salt, and Lipoid E 80 S.

E36. The pharmaceutical composition according to any of embodiments E27 to E35, further comprising one or more solvents, in particular those solvents described in any of embodiments E8, E9 or E10.

E37. The pharmaceutical composition according to any of embodiments E27 to E36, further comprising a stabiliser selected from sodium chloride, potassium chloride, sodium phosphate di- and monobasic, ammonium sulphate and arginine, preferably sodium chloride.

E38. The pharmaceutical composition according to any of embodiments E27 to E37, further comprising a tonicity adjusting agent.

E39. The pharmaceutical composition according to embodiment E38, wherein the tonicity adjusting agent is selected from dextrose, glucose, mannitol, sucrose, lactose, trehalose, glycerine and NaCl, in particular sucrose and/or glycerine, more particularly sucrose.

E40. The pharmaceutical composition according to any of embodiments E27 to E39, further comprising a buffer, in particular histidine.

E41. A pharmaceutical composition according to any of embodiments E27 to E40, comprising liposomes.

E42. A pharmaceutical composition according of any of embodiments E27 to E41, wherein the ratio of phospholipid (from the liposomal vehicle) to Compound A as the free molecule, is from 100:1 to 4.5:1 parts by weight.

E43. A pharmaceutical composition according to embodiment E42, wherein the ratio of phospholipid from the liposomal vehicle to Compound A as the free molecule, is from 50:1 to 6:1 parts by weight, in particular from 20:1 to 9:1 parts by weight.

E44. A pharmaceutical composition according to any of embodiments E27 to E43, wherein the loaded liposomes have an average size of from 20 nm to 100 nm, in particular from 50 nm to 90 nm, more particularly from 50 nm to 80 nm.

E45. A pharmaceutical composition for infusion or intravenous injection comprising a mixture of the liposomal vehicle according to any of embodiments E13 to E26, and the organic concentrate composition according to any of embodiments E1 to E12.

E46. A pharmaceutical composition for infusion according to embodiment E45, further comprising glucose for infusion.

E47. An organic concentrate composition comprising:
a. Compound A which is (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid,
b. a negatively charged or polar phospholipid stabiliser, and
c. at least one solvent selected from propylene glycol, ethanol, PEG300 and PEG400.

E48. An organic concentrate composition according to embodiment E47, comprising propylene glycol, ethanol and PEG300, in particular both propylene glycol and ethanol.

E49. An organic concentrate composition according to embodiments E47 or E48, further comprising a stabiliser selected from sodium chloride, potassium chloride, sodium phosphate di- and monobasic, ammonium sulphate and arginine, in particular sodium chloride.

E50. A pharmaceutical composition for infusion or intravenous injection comprising:
a. a phospholipid selected from those described in any one of embodiments E15 to E19,
b. Compound A which is (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2{[2-(2-methoxyphenyl)pyrimidin-4-yl]methoxy}phenyl)propanoic acid, and
c. a negatively charged or polar phospholipid stabiliser selected from those described in any of embodiments E4 to E6.

E51. A pharmaceutical composition according to embodiment E50, further comprising a stabiliser selected from sodium chloride, potassium chloride, sodium phosphate di- and monobasic, ammonium sulphate and arginine, in particular sodium chloride.

E52. A pharmaceutical composition according to embodiments E50 or E51, further comprising both propylene glycol and ethanol.

E53. A kit comprising:
a. the liposomal vehicle according to any one embodiments E13 to E26, and
b. the organic concentrate composition according to any one embodiments E1 to E12, or E47 to E49, or E55 to E66, E81 or E82.

E54. A kit according to embodiment E53, wherein a. and b. are intended to be mixed with each other immediately prior to administration to the patient.

E55. An organic concentrate composition comprising:
a. Compound A which is 2-{[5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid, or a pharmaceutically acceptable salt thereof,
b. a negatively charged or polar phospholipid stabiliser, and
c. a stabiliser against jellification.

E56. An organic concentrate composition according to embodiment E55, comprising Compound A which is (2R)-2-{[(5$S_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof.

E57. An organic concentrate composition according to embodiment E55 or E56, wherein Compound A is the free molecule.

E58. An organic concentrate composition according to any of embodiments E55 to E57, wherein the negatively charged or polar phospholipid stabiliser is selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, egg lecithin (for example Lipoid E 80 S), soy lecithin (for example Lipoid S 75), and sodium oleate, preferably DMPG sodium salt.

E59. An organic concentrate composition according to embodiment E58, wherein the negatively charged or polar phospholipid stabiliser is 1,2-Dimyristoyl-sn-glycero-3-phospho-rac-glycerol, sodium or ammonium salt, egg lecithin (for example Lipoid E 80 S), soy lecithin (for example Lipoid S 75), or, preferably 1,2-Dimyristoyl-sn-glycero-3-phospho-rac-glycerol, sodium salt.

E60. An organic concentrate composition according to any of embodiments E55 to E59, wherein the stabiliser against jellification is a polymer or an electrolyte.

E61. An organic concentrate according to embodiment E60, wherein the stabiliser against jellification is an electrolyte selected from sodium chloride, potassium chloride, sodium phosphate di- and monobasic, ammonium sulphate and arginine, in particular sodium chloride, potassium chloride, sodium phosphate di- and monobasic, and ammonium sulphate.

E62. An organic concentrate composition according to embodiment E61, wherein the stabiliser against jellification is sodium chloride.

E63. An organic concentrate composition according to embodiment E60, wherein the stabiliser against jellification is a polymer selected from PEG300 and PEG400, preferably PEG300.

E64. An organic concentrate composition according to embodiment E63, wherein PEG300 is present at from 5% w/w to 30% w/w of the concentrate composition, in particular from 15% w/w to 20% w/w more particularly 15% w/w.

E65. An organic concentrate composition according to any of embodiments E55 to E64, further comprising a solvent.

E66. An organic concentrate composition according to embodiment E65, further comprising a solvent selected from propylene glycol and ethanol, and in particular comprising both propylene glycol and ethanol.

E67. A pharmaceutical composition resulting from the mixture of the organic concentrate composition according to any of embodiments E1 to E12, or E47 to E49, or E55 to E66, and a liposomal vehicle, wherein said liposomal vehicle comprises a phospholipid and a tonicity adjusting agent, in particular wherein said tonicity adjusting agent is selected from dextrose, glucose, mannitol, sucrose, lactose, trehalose, glycerine and NaCl.

E68. A pharmaceutical composition according to embodiment E67, wherein the phospholipid is of the formula

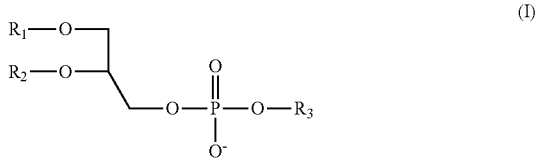

wherein
R₁ represents $C_{10}$-$C_{24}$acyl;
R₂ represents $C_{10}$-$C_{24}$acyl, or alternatively, R₂ represents hydrogen or $C_{10}$-$C_{20}$acyl;
R₃ represents hydrogen, 2-trimethylamino-1-ethyl, 2-amino-1-ethyl, $C_1$-$C_4$alkyl, $C_1$-$C_5$alkyl substituted by carboxy, $C_2$-$C_5$alkyl substituted by carboxy and hydroxy, $C_2$-$C_5$alkyl substituted by carboxy and amino, an inositol group or a glyceryl group;
or a salt of such compound.

E69. A pharmaceutical composition according to embodiment E67, wherein the phospholipid is selected from egg lecithin, soy lecithin, or synthetic phospholipids.

E70. A pharmaceutical composition according to embodiments E67 to E69, wherein the phospholipid is selected from egg lecithin, soy lecithin, POPC (palmitoyl oleoyl phosphatidylcholine), DOPC (1,2-Dioleoyl-sn-glycero-3-phosphocholine), DMPC (1,2-Dimyristoyl-sn-glycero-3-phosphocholine) and DPPC (1,2-Dipalmitoyl-sn-glycero-3-phosphocholine), especially POPC (palmitoyl oleoyl phosphatidylcholine), DOPC (1,2-Dioleoyl-sn-glycero-3-phosphocholine), and DMPC (1,2-Dimyristoyl-sn-glycero-3-phosphocholine), in particular POPC.

E71. A pharmaceutical composition according to any of embodiments E67, E69 or E70, wherein the phospholipid is selected from egg lecithin or soy lecithin comprising at least 75% phosphatidylcholine, or at least 70% phosphatidylcholine, and in particular is selected from Lipoid E 80 S.

E72. A pharmaceutical composition according to any of embodiments E67 to E71, wherein the tonicity adjusting agent is selected from dextrose, glucose, mannitol, sucrose, lactose, trehalose, glycerine and NaCl, particularly sucrose or glycerine.

E73. A liposomal pharmaceutical composition comprising, in addition to liposomes:
a. Compound A which is 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid, or a pharmaceutically acceptable salt thereof; and
b. a stabiliser against jellification.

E74. A liposomal pharmaceutical composition according to embodiment E73, comprising:
a. Compound A as described in any of embodiments E2 to E3, and
b. a stabiliser against jellification, as described in any of embodiments E60 to E63.

E75. A liposomal pharmaceutical composition according to embodiment E74, further comprising a negatively charged or polar phospholipid stabiliser.

E76. A liposomal pharmaceutical composition according to embodiment E75, wherein said negatively charged or polar phospholipid stabiliser is as described in E4 to E6 or E58 or E59.

E77. A liposomal pharmaceutical composition according to any of embodiments E73 to E76, further comprising a solvent.

E78. A liposomal pharmaceutical composition according to embodiment E77, wherein said solvent is selected from propylene glycol and ethanol, or in particular comprising both propylene glycol and ethanol.

E79. A liposomal pharmaceutical composition according to any of embodiments E73 to E78, comprising a phospholipid as described in any of embodiments E15 to E19, or any of embodiments E68 to E71.

E80. A liposomal pharmaceutical composition according to any of embodiments E73 to E79, further comprising a tonicity adjusting agent, in particular wherein said tonicity adjusting agent is selected from dextrose, glucose, mannitol, sucrose, lactose, trehalose, glycerine and NaCl.

E81. An organic concentrate composition comprising;
a. Compound A which is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof, preferably the free molecule,
b. a negatively charged or polar phospholipid stabiliser, for example selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, Lipoid E 80 S, and sodium oleate, and
c. a stabiliser selected from sodium chloride, potassium chloride, sodium phosphate di- and monobasic, ammonium sulphate and arginine, preferably sodium chloride.

E82. An organic concentrate composition comprising:
a. Compound A which is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid,
b. a negatively charged or polar phospholipid stabiliser, for example selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, egg lecithin (for example Lipoid E 80 S), soy lecithin (for example Lipoid E75), and sodium oleate, especially DMPG sodium; and
c. a stabiliser against jellification, for example selected from
  a polymer, wherein said polymer is in particular PEG300 and PEG400, and
  an electrolyte, wherein said electrolyte is in particular sodium chloride, potassium chloride, sodium phosphate di- and monobasic, ammonium sulphate and arginine, more particularly sodium chloride, potassium chloride, sodium phosphate di- and monobasic, ammonium sulphate, especially sodium chloride E83. A pharmaceutical composition comprising:
a. a phospholipid selected from egg lecithin, soy lecithin, POPC (palmitoyl oleoyl phosphatidylcholine), DOPC (1,2-Dioleoyl-sn-glycero-3-phosphocholine), DMPC (1,2-Dimyristoyl-sn-glycero-3-phosphocholine) and DPPC (1,2-Dipalmitoyl-sn-glycero-3-phosphocholine), especially POPC (palmitoyl oleoyl phosphatidylcholine), DOPC (1,2-Dioleoyl-sn-glycero-3-phosphocholine), and DMPC (1,2-Dimyristoyl-sn-glycero-3-phosphocholine), in particular POPC,
or wherein the phospholipid is selected from egg lecithin or soy lecithin comprising at least 70% phosphatidylcholine;
b. Compound A which is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid or a salt thereof, preferably the free molecule,
c. a negatively charged or polar phospholipid stabiliser, for example DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, Lipoid E 80 S, and sodium oleate, especially 1,2-Dimyristoyl-sn-glycero-3-phospho-rac-glycerol, sodium or ammonium salt, egg lecithin or Lipoid E 80 S, preferably 1,2-Dimyristoyl-sn-glycero-3-phospho-rac-glycerol, sodium salt; and
d. a stabiliser against jellification, for example selected from
  a polymer, wherein said polymer is in particular PEG300 and PEG400, and
  an electrolyte, wherein said electrolyte is in particular sodium chloride, potassium chloride, sodium phosphate di- and monobasic, ammonium sulphate and arginine, more particularly sodium chloride, potassium chloride, sodium phosphate di- and monobasic, ammonium sulphate, especially sodium chloride.

E84. A process for solubilizing Compound A, as described in any of embodiments E1, E2 or E3, in an aqueous environment, comprising mixing:
  a. the liposomal vehicle according to any of embodiments E13 to E26, and
  b. the organic concentrate composition according to any of embodiments E1 to E12, or E47 to E49, or E55 to E66, E81 or E82.

E85. A process for preparing a composition of Compound A suitable for parenteral administration, comprising mixing:
  a. the liposomal vehicle according to any of embodiments E13 to E26, and
  b. the organic concentrate composition according to any of embodiments E1 to E12 or E47 to E49, or E55 to E66, E81 or E82.

E86. A process according to embodiment E84 or E85, wherein the mixing takes place immediately prior to administration to the patient.

E87. A process according to any of embodiments E84, E85 or E86, wherein the mixing and liposome loading is performed by repeated inversion, in particular shaking vigorously by inversion, of the container.

E88. A process according to any of embodiments E84 to E87, wherein the mixing and liposome loading is performed by inverting a container containing both a. and b, in particular repeatedly, or shaking vigorously by inversion, until the mixture is free of visual particles.

E89. A method of modulating Mcl-1 receptor activity in a subject, wherein the method comprises administering to the subject a therapeutically effective amount of the composition according to any of embodiments E27 to E46, or E50 to E52, or E67 to E80, or E83.

E90. A method of treating cancer, comprising administering to the subject a therapeutically effective amount of the composition according to any of embodiments E27 to E46, or E50 to E52, or E67 to E80, or E83.

E91. A method according to embodiment E90, wherein the cancer is selected from cancers of the bladder, brain, breast and uterus, chronic lymphoid leukaemias, cancer of the colon, œsophagus and liver, lymphoblastic leukaemias, acute myeloid leukaemia, lymphomas, for example non-Hodgkin's B-cell lymphoma and diffuse large B-cell lymphoma, melanomas, malignant haemopathies, for example myelodysplastic syndrome, myelomas, for example multiple myeloma, ovarian cancer, non-small-cell lung cancer, prostate cancer, pancreatic cancer and small-cell lung cancer.

E92. A method according to embodiment E91, wherein the cancer is selected from non-Hodgkin's B-cell lymphoma, diffuse large B-cell lymphoma, multiple myeloma, myelodysplastic syndrome, chronic lymphoid leukaemias and acute myeloid leukemia.

E93. A pharmaceutical composition according to any of embodiments E27 to E46, or E50 to E52, or E67 to E80, or E83, for use as a medicament.

E94. A pharmaceutical composition for use according to embodiment E93, wherein said use is in the treatment of cancer, in particular wherein cancer is selected from cancers of the bladder, brain, breast and uterus, chronic lymphoid leukaemias, cancer of the colon, cesophagus and liver, lymphoblastic leukaemias, acute myeloid leukaemia, lymphomas, for example non-Hodgkin's B-cell lymphoma and diffuse large B-cell lymphoma, melanomas, malignant haemopathies, for example myelodysplastic syndrome, myelomas, for example multiple myeloma, ovarian cancer, non-small-cell lung cancer, prostate cancer, pancreatic cancer and small-cell lung cancer.

E95. A pharmaceutical composition for use according to embodiment E94, wherein said cancer is selected from non-Hodgkin's B-cell lymphoma, diffuse large B-cell lymphoma, multiple myeloma, myelodysplastic syndrome, chronic lymphoid leukaemias and acute myeloid leukemia.

E96. Use of an organic concentrate composition according to any of embodiments E1 to E12 or E47 to E49, or E55 to E66, E81 or E82, for the preparation of a medicament to treat cancer.

E97. Use according to embodiment E96, for the preparation of liposomal medicament to treat cancer.

E98. The use according to embodiment E96 or E97, wherein the cancer is selected from cancers of the bladder, brain, breast and uterus, chronic lymphoid leukaemias, cancer of the colon, œsophagus and liver, lymphoblastic leukaemias, acute myeloid leukaemia, lymphomas, for example non-Hodgkin's B-cell lymphoma and diffuse large B-cell lymphoma, melanomas, malignant haemopathies, for example myelodysplastic syndrome, myelomas, for example multiple myeloma, ovarian cancer, non-small-cell lung cancer, prostate cancer, pancreatic cancer and small-cell lung cancer, in particular non-Hodgkin's B-cell lymphoma, diffuse large B-cell lymphoma, multiple myeloma, myelodysplastic syndrome, chronic lymphoid leukaemias and acute myeloid leukemia.

E99. A combination comprising:
a pharmaceutical composition according to any of embodiments E27 to E46, or E50 to E52, or E67 to E80, or E83, and
one or more therapeutically active agents, for simultaneous, sequential or separate use.

E100. A composition comprising Compound A, as defined in E1, E2 or E3, and a stabiliser against jellification.

In a particular embodiment, the patients are selected, for example according to the following criteria:
Principal Inclusion Criteria:
Age ≥18 years
For patients with multiple myeloma:
Histologically confirmed lymphoma or confirmed multiple myeloma. In a particular embodiment for multiple myeloma patients, the multiple myeloma is relapsed and/or refractory to standard treatment
Chromosomal aberration characterized
Measurable disease:
Serum M-protein ≥0.5 g/dl
Urine M-protein ≥200 mg/24 hours or
Serum free light chain (FLC) level ≥100 mg/L of involved FLC.
For patients with histologically confirmed DLBCL:
Documented MYC positivity defined by Fluorescence in situ hybridization (FISH) or immunohistochemistry (IHC)
Measurable disease (according Recommendations for Initial Evaluation, Staging, and Response Assessment of Hodgkin and Non-Hodgkin Lymphoma)
Principal Exclusion Criteria
1. Known history of chronic liver disease including active hepatitis B or C infection
primary biliary cirrhosis
cirrhosis of the liver, or
portal hypertension
2. History of chronic pancreatitis
3. Patients with high risk of tumor lysis syndrome (TLS)
4. History or diagnosis of pneumonitis, interstitial lung disease or inflammatory bowel disease.

5. Impaired cardiac function or clinically significant cardiac diseases, including any of the following:
Left ventricular ejection fraction (LVEF)<50% as determined by multiple gated acquisition scan (MUGA) or echocardiogram (ECHO)
QT corrected with Fredericia's (QTcF)>450 ms (male patients), >460 ms (female patients)
6. Severe and/or uncontrolled medical conditions that in the investigator's opinion could affect the safety of the individual or impair the assessment of study result.
7. Prior treatment with Mcl-1 inhibitor.
8. Prior treatment with Bcl-2 inhibitor (for patients enrolled in dose expansion).
9. Patients with a primary CNS tumor or CNS tumor involvement.

The liposomal vehicle described herein may be produced by any production method resulting in liposomes with an average particle size of up to 1000 nm, preferably up to 300 nm, in particular up to 100 nm. The liposome size as described herein refers to the Z average diameter using photon correlation spectroscopy according ISO 13321 which describes the resulting average particle size and the polydispersity index. A typical production method includes dispersing, high shear mixing and subsequent high pressure homogenization and such methods are well known to the skilled person.

The organic concentrate is formed by mixing the components until a homogeneous solution is obtained in which Compound A is dissolved.

To form the composition for administration, the concentrate is added to the liposomal vehicle, then immediately mixed, for example by repeated inversion, or vigorous shaking. Alternatively, the concentrate can be added to the vehicle while swirling.

Advantageously, in a particular embodiment of the invention, there is provided a liposomal vehicle which can be mixed with Compound A shortly before administration to produce a transparent composition. In particular, this is achieved by the mixing of the liposomal vehicle with the organic concentrate comprising Compound A as described herein. Transparency is desirable in order to check that Compound A is solubilized prior to administration. This may be judged by visual inspection, or the clarity is determined at the most appropriate wave length depending on the lipid concentration, for example 660 nm or using a 1 cm transmission cell or cuvette. In an aspect of the invention, the pharmaceutical composition for administration (liposomes loaded with Compound A) should not decrease transmission compared to the liposomal vehicle by more than 30%, preferably not more than 20%, most preferably not more than 10%.

In a preferred embodiment of the invention, the liposome vehicle, when mixed with Compound A, enables maximum loading of Compound A into the liposomes, in particular when Compound A is present as the organic concentrate described herein.

In the Examples herein, 'Compound A' means (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (no salt).

Example 1: Organic Concentrate Comprising Compound A and Sodium Chloride

| Composition | Composition per mL [mg] | Excipient function |
|---|---|---|
| Compound A | 61.75 | |
| DMPG-Na (1,2-Dimyristoyl-sn-glycero-3-phospho-rac-glycerol, sodium salt) | 3.83 | stabiliser |
| Ethanol, anhydrous | 94.39 | solvent |
| Sodium chloride | 4.00 | stabiliser |
| Water for injection | 9.58 | solvent |
| Propylene glycol | 851.41 | solvent |

Preparation of Bulk Solvent

Water for injection followed by anhydrous ethanol, then DMPG-Na are charged to a vessel and stirred to wet the DMPG-Na powder. Approximately a quarter of the propylene glycol is then added, and the mixture stirred and warmed. Stirring is continued and the temperature maintained for 90 minutes or until complete dissolution of the DMPG-Na.

After complete dissolution, the mixture is then cooled to room temperature, the remainder of the propylene glycol is added and the mixture stirred until it appears homogeneous. Sodium chloride is then added, and the mixture warmed for 90 minutes or until complete dissolution of the sodium chloride. The resulting solution is cooled to room temperature.

Preparation of Organic Drug Concentrate

Bulk solvent prepared as described above is charged to a vessel, Compound A added and the mixture stirred to wet the Compound A powder. Stirring is continued for 60 minutes or until complete dissolution of Compound A. The concentrate is filtered through a sterile 0.2 μm Pall Fluorodyne® II DFL Membrane in Kleenpak™ Capsules KA3DFLP1G or KA3DFLP1. After filtration, the resulting organic drug product concentrate (61.75 mg/ml) is transferred to sterile, depyrogenated vials.

Example 2: Liposomal Vehicle for Dilution

| Excipient | Composition per mL [mg] | Excipient function |
|---|---|---|
| Sucrose | 90 | tonicity adjusting agent |
| ePL, Lipoid E 80 S (Egg phospholipids) | 100 | solubilizer |
| L-Histidine | 1.5 | buffer |
| Hydrochloric acid | If required to pH 6.5 | pH adjusting agent |
| Sodium hydroxide | If required to pH 6.5 | pH adjusting agent |
| Water for injection | Qs to 1 mL | solvent |

Preparation of the Liposomal Vehicle for Dilution

As the Lecithin (ePL) is prone to oxidation, the oxygen is removed wherever technically possible and the materials are preferably to be protected by a nitrogen overlay.

Water for injection, followed by L-Histidine, are charged to a vessel and stirred until L-Histidine is completely dissolved. Sucrose is charged and the mixture stirred until the sucrose is completely dissolved. The pH is checked and adjusted to 6.5±0.2 by addition of 1N hydrochloric acid or 1N sodium hydroxide solution, then solution is stirred until homogeneous. Lipoid E 80 S is then added to the vessel. The mixture is stirred until a homogeneous dispersion is obtained.

In Line Mixing

The dispersion obtained above is stirred and transferred to another vessel via an in line homogenizer (Kinematica MEGATRON MT-SV 1-45 M), regulated to a flow of 2-5 L/min. The in line mixing is continued until the source vessel is empty.

High Pressure Homogenization

The vessel containing the lecithin dispersion obtained above is connected to a high pressure homogenizer (Avestin Emulsiflex C160) in a recirculation loop, and the dispersion cooled to 2-8° C. while stirring at 300 rpm. After pressuring the vessel to 0.5 bar, the pump is set to maximum speed and the high pressure homogenizer primed with open valve to remove air in the system. The high pressure homogenizer pump is then set to 60 Hz, the flow to 130-140 L/h and the pressure to 950 to 1050 bar, and high pressure homogenization performed for 19 passes (ca 7.5-8 hours), then at the $20^{th}$ pass, the content of the vessel is transferred to another vessel via the high pressure homogenizer.

A pre-filtration is performed with a PVDF (polyvinylidene difluoride membrane) 0.2 μm filter, and the filtered solution is stored at room temperature. Then the solution is sterile filtered through a PVDF sterilizing grade filter and then transferred to sterile vials depyrogenated by dry heat treatment.

This aqueous formulation can be injected or infused as such or diluted with infusion solutions (e.g. 5% Glucose) before being infused.

Example 3A: Formulation for Infusion

The organic concentrate from Example 1 is mixed with the liposomal vehicle from Example 2 as follows. The liposomal vehicle from Example 2 is allowed to warm to room temperature (i.e. 20 to 25° C.) by taking it out of the refrigerator at least 30 minutes prior to mixing. The total volume of active liposomal vehicle which will be administered to the patient can be determined as indicated in Table 3A.1 below. The liposomal vehicle contains small liposomes and is used as a solubilizing vehicle, able to dissolve Compound A in an aqueous environment after mixing with the organic concentrate comprising compound A.

TABLE 3A.1

| Required dose of Compound A mg | Number of vials needed of the Drug product (Compound A concentrate for infusion) and liposomal vehicle for dilution (LV) # | Total volume of active liposomal vehicle (concentration of Compound A 7.5 mg/ml) to be transferred into the glucose bag ml | Syringe size/scaling | Concentration of Compound A in 250 mL bag ready for infusion (Note: bag overfill not considered) mg/ml |
|---|---|---|---|---|
| 30 | 1 | 4.0 | 5 mL/0.2 mL | 0.12 |
| 45 | 1 | 6.0 | 10 mL/0.5 mL | 0.18 |

TABLE 3A.1-continued

| Required dose of Compound A mg | Number of vials needed of the Drug product (Compound A concentrate for infusion) and liposomal vehicle for dilution (LV) # | Total volume of active liposomal vehicle (concentration of Compound A 7.5 mg/ml) to be transferred into the glucose bag ml | Syringe size/ scaling | Concentration of Compound A in 250 mL bag ready for infusion (Note: bag overfill not considered) mg/ml |
|---|---|---|---|---|
| 180 | 1 | 24.0 | 30 mL/0.5 mL | 0.72 |
| 360 | 2 | 48.0 | 30 mL/0.5 mL | 1.44 |
| 540 | 3 | 72.0 | 30 mL/0.5 mL | 2.16 |
| 720 | 4 | 96.0 | 30 mL/0.5 mL | 2.88 |
| 900 | 5 | 120.0 | 30 mL/0.5 mL | 3.60 |
| 1080 | 6 | 144.0 | 30 mL/0.5 mL | 4.32 |
| 1260 | 7 | 168.0 | 30 mL/0.5 mL | 5.04 |
| 1400 | 8 | 186.7 | 30 mL/0.5 mL | 5.60 |
| X [mg] | To be determined based on dose to be administered and nominal content of Compound A of 180 mg/vial of drug product (Compound A concentrate for infusion) | =X [mg]/7.5 mg/ml | See above. Select syringe size/ scaling closest to the value of total volume of active liposomal vehicle given in the table | =X [mg]/250 ml |

One vial of Compound A organic concentrate (185.25 mg [including overage] Compound A in 3 mL) is combined with one vial of the liposomal vehicle (2.1 gram of Lipoid E 80 S in 21 mL), to obtain a withdrawable volume of 24 mL active liposomal vehicle comprising Compound A containing a total of 180 mg of Compound A). For one patient more vials may need to be prepared. The adequate number of vials of active liposomal vehicle sufficient to dose the patient must be prepared.

Compound A organic concentrate (3 mL) is aseptically and accurately withdrawn and injected quickly into one vial of the liposomal vehicle and immediately mixed by inverting the vial ≥40 times. An initial cloudiness will disappear. The resulting active liposomal vehicle formulation will be slightly more turbid compared to the liposomal vehicle for dilution. It must be free of visual particles after mixing. If more than 180 mg of Compound A needs to be administered to the patient, the addition and mixing step is repeated as required.

The total volume of glucose solution to be removed from an infusion bag is then calculated (for example, using Glucose 5% Ecobag, or Glucose 5% Ecoflac). This volume is the same as the volume of active liposomal vehicle as given in Table 3A.1. The calculated volume of glucose solution is aseptically and accurately withdrawn from the infusion bag (and discarded).

The calculated volume of active liposomal vehicle (comprising Compound A) is aseptically and accurately withdrawn from one or more vials and injected into the glucose bag prepared above, and mixed well by inverting the bag at least 10 times. If less than a multiple of 180 mg of Compound A is needed, the residual in the vials needs to be discarded.

The prepared infusion bag ready for infusion must be inspected visually for particulate matter. The content of the bag may appear opalescent or slightly turbid depending on the Compound A concentration. If particles are visible, the bag is discarded and a fresh infusion bag prepared.

Compound A is slightly sensitive to light, so the infusion bag is placed in a light protection cover.

One example of a procedure is as follows. Freshly prepared infusion bags are stored for up to 5 hours at room temperature (i.e. 20 to 25° C.) plus up to 8 hours under refrigerator conditions (2 to 8° C.) which includes the actual time of infusion. If kept at room temperature 20 to 25° C., the diluted solution for infusion in the infusion bag can be prepared and infusion started within two hours after preparation and administered at controlled room temperature. If the intravenous solution is not administered immediately, the solution can be refrigerated at 2 to 8° C. for less than 8 hours only. If the prepared solution is refrigerated prior to administration, the bag can be brought up to room temperature prior to administration. The infusion formulation containing the required concentration of Compound A drug product can be infused through an infusion line and a 1.2 µm in-line filter after the infusion bag, being located as close as possible to the catheter.

Example 3B: Formulation for Infusion

Using the same procedure as Example 3A, the liposomal vehicle from Example 2 was mixed with an organic solution of the following composition:

| Description | Composition per ml [mg] | Excipient Function |
|---|---|---|
| Compound A | 100 | |
| Lipoid E 80 S | 18.54 | stabiliser |
| Propylene Glycol | 410.73 | solvent |
| Ethanol | 410.73 | solvent |

The following mixing ratios can be used:

| Required concentration Compound A (mg/mL) | Required volume of the active liposomal formulation (mL) | Volume of the organic solution (mL) | Volume of the liposomal vehicle (mL) |
|---|---|---|---|
| 0.00 | 80 | 0.00 | 80.00 |
| 0.30 | 65 | 0.20 | 64.80 |
| 0.60 | 83.5 | 0.50 | 83.00 |
| 0.75 | 80 | 0.60 | 79.40 |
| 1.50 | 80 | 1.20 | 78.80 |
| 2.50 | 80 | 2.00 | 78.00 |

-continued

| Required concentration Compound A (mg/mL) | Required volume of the active liposomal formulation (mL) | Volume of the organic solution (mL) | Volume of the liposomal vehicle (mL) |
|---|---|---|---|
| 3.00 | 80 | 2.40 | 77.60 |
| 3.75 | 80 | 3.00 | 77.00 |
| 5.00 | 80 | 4.00 | 76.00 |
| 7.50 | 80 | 6.00 | 74.00 |

Example 4: Efficacy of Compound A Liposomal Formulation in MV4;11 Acute Myeloid Leukemia Xenograft Model in Nude Rats Using a Once a Week Intravenous Administration Schedule Methods

TABLE 4.1

Organic solvent composition used for preparing the dosing solution for the vehicle group:

| Ingredient | Composition per mL [mg] |
|---|---|
| Egg lecithin Lipid E 80 S | 20 |
| Propylene glycol | 443.0 |
| Ethanol | 443.0 |

TABLE 4.2

Composition of liposomal vehicle used for preparing the dosing solution for the vehicle group:

| Ingredient | Composition per mL [mg] |
|---|---|
| Egg lecithin Lipid E 80 S | 100 |
| Sucrose | 90 |
| L-Histidine | 1.552 |
| Water for injection | q.s to 1.00 mL |

The liposomal vehicle was obtained using the components of Table 4.2 and methods described herein in Example 2. The organic solution (Table 4.1) was mixed with the liposomal vehicle in 1:32.33 (v/v) ratio and used to dose the vehicle group at 10 mL/kg.

This study evaluated the antitumor activity and tolerability of Compound A in a liposome based formulation after i.v. infusion in MV4;11 tumor bearing nude rats. Experiments were performed in female Crl:NIH-Foxn1rnu nude rats (Charles River).

MV4;11 luc human acute myeloid leukemia (AML) cell line was established from the parental MV4;11 cells which were derived from a patient. The parental MV4;11 cells were obtained from the DSMZ cell bank. The MV4;11 luc cells were used for all in vivo studies and were cultured in RPMI-1640 medium (BioConcept Ltd. Amimed, #1-41F01-I) supplemented with 10% FCS (GE health care life sciences, # H30071.03) 4 mM L-glutamine (BioConcept Ltd. Amimed, #5-10K00-H), 0.6 mg/ml geneticin (Life Technologies, #10131-027) at 37° C. in an atmosphere of 5% $CO_2$ in air. Cells were maintained between 0.2 and $1.1 \times 10^6$ cells/mL. To establish MV4;11 luc xenografts cells were harvested and re-suspended in HBSS (Gibco, #14175) and mixed with Matrigel (BD Bioscience, #354234) (1:1 v/v) before injecting 200 μL containing $1 \times 10^7$ cells subcutaneously in the right flanks of animals which were anesthetized with isoflurane. Twenty four hours prior to cell inoculation all animals were irradiated with 5 Gy over 2 minutes using a γ-irradiator.

Tumor growth was monitored regularly post cell inoculation and animals were randomised into treatment groups when their tumors reached appropriate volume. Tumor size, in $mm^3$, was calculated from: $(L \times W2 \times \pi/6)$ where W=width and L=length of the tumor.

Tumor bearing animals were enrolled into treatment groups (n=5) with a mean tumor volume of about 450 $mm^3$. Animals were then treated with the vehicle or Compound A formulation at a dose of 10 and 30 mg/kg.

Compound A was formulated in liposome based formulation using the organic drug concentrate (described in Example 1) and vehicle (described in Example 2 herein). The dosing solutions were formed by mixing the product of Examples 1 and 2 at 1:7.236 (v/v) then further diluting this mixture by adding 5% glucose at 1:6.50 (v/v) for 10 mg/kg dose and 1:1.50 (v/v) for 30 mg/kg dose.

The vehicle and Compound A were administered once a week (QW) by i.v. 15 minutes infusion in the lateral tail vein at 10 mL/kg. Animals were anesthetized with isoflurane/$O_2$ for about 20 minutes to perform the infusion. Tumor volumes were measured using calipers 2-3 times per week. Animals were weighed 2-3 times per week and examined frequently for overt signs of any adverse effects.

Tumor and body weight change data were analyzed statistically using GraphPad Prism 7.00 (GraphPad Software). If the variances in the data were normally distributed, the data were analyzed using one-way ANOVA with post hoc Dunnett's test for comparison of treatment versus control group. The post hoc Tukey's test was used for intragroup comparison. Otherwise, the Kruskal-Wallis ranked test post hoc Dunn's was used. When applicable, results are presented as mean±SEM.

As a measure of efficacy the % T/C value is calculated at the end of the experiment according to:

$$(\Delta tumor\ volume^{treated}/\Delta tumor\ volume^{control})*100$$

Tumor regression was calculated according to:

$$-(\Delta tumor\ volume^{treated}/tumor\ volume^{treated\ at\ start})*100$$

where Δtumor volumes represent the mean tumor volume on the evaluation day minus the mean tumor volume at the start of the experiment.

Results: Efficacy and Tolerability

Figure 2:
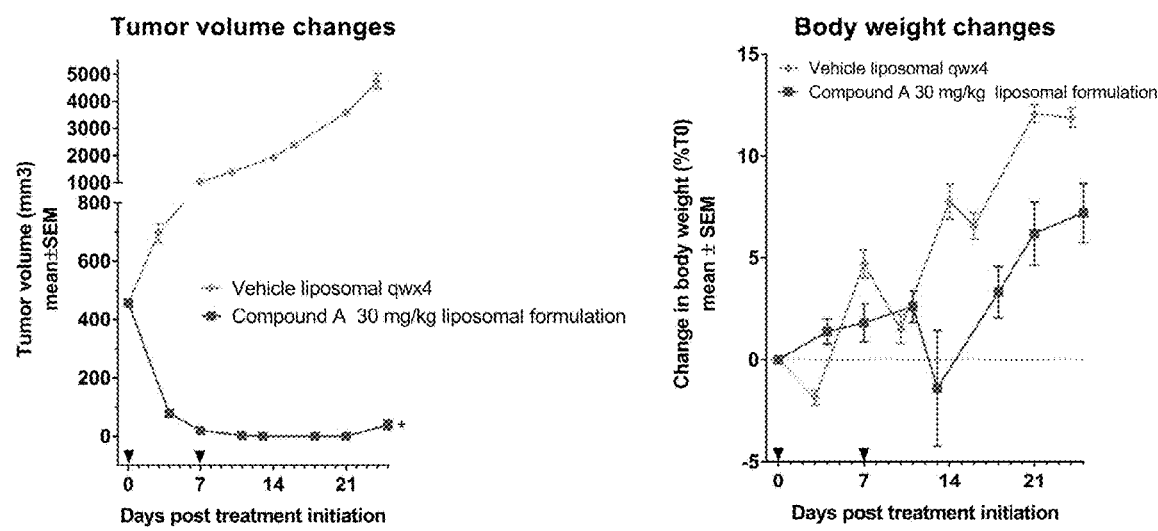
FIG. 2 shows the efficacy and tolerability of liposomal formulated Compound A after 30 mg/kg QW administration in female nude rats bearing MV4;11 AML xenografts.

The liposome based Compound A formulation exhibited significant dose-related efficacy after infusion administration. A 10 mg/kg QW infusion dose, induced maximum antitumor response after the first dose (61% regression on day 3 post start of treatment) and the response was attenuated in each subsequent dose, leading to a gradual increase in tumor volume with time. On day 24 (the last day of tumor volume measurement in the vehicle group) the regression was 6% after a 10 mg/kg QW dose (p<0.05 compared with vehicle group). After infusion of 30 mg/kg Compound A liposomal formulation QW for 2 weeks, complete regression (CR) was achieved in all MV4;11 xenografts on day 13 post start of treatment. Complete regression was maintained in all animals up to day 21 after which tumor regrowth was observed in 3 animals and 2 animals showed no tumor growth for a further 60 days after reaching CR. On day 25 post start of treatment with 30 mg/kg, the mean tumor volume showed 92% regression (p<0.05 compared with vehicle group). Based on body weight changes both dosing regimens of the liposomal formulation were well tolerated. Results are shown in FIGS. 1 and 2.

Example 5: Stability Data for the Composition of Example 1

The stability of the composition of Example 1, Compound A 185.25 mg in 3.0 mL was investigated, by testing storage periods of up to 3 months, and photostability.

5.1. Testing at 5° C./Ambient RH (Relative Humidity)

During 3 months storage in vials at conditions 5° C./ambient RH, Example 1 composition Compound A 185.25 mg/3.0 mL was observed to be physically and chemically stable. No significant changes in chemical or physical properties were observed.

5.2. Testing at 25° C./60% RH

During 3 months storage in vials at conditions 25° C./60% RH, Example 1 composition Compound A 185.25 mg/3.0 mL was observed to be physically stable. No significant changes were observed for 3 months. Increased levels of undesired atropisomer were observed. All results remained within specification limits.

5.3. Testing at 40° C./75% RH

During 3 months storage in vials at conditions 40° C./75% RH, Example 1 composition Compound A 185.25 mg/3.0 mL was observed to be physically stable. No significant changes were observed for 3 months, except for increased levels of undesired atropisomer with time. All results were within specification limits after 1.5 months.

5.4. Photostability

During photostability test in vials, Example 1 composition Compound A 185.25 mg/3.0 mL was observed to not be chemically nor physically stable. All results for the sample protected from light exposure were observed within specification limits.

Conclusions

Satisfactory stability data have been achieved for 3 months at 5° C./ambient RH and 25° C./60% RH and 1.5 months at 40° C./75% RH. The available stability data indicate satisfactory stability of Example 1 composition Compound A 185.25 mg/3.0 mL. Protection from light will be necessary.

Example 6: Stability Data for the Composition of Example 2

The stability of the composition of Example 2 vehicle (21.7 mL) was investigated, by testing storage periods of up to 3 months, and photostability 6.1. Testing at 5° C./Ambient RH No changes were observed in appearance of the container, appearance of the content and quantification of phospholipids up to 3 months stored at 5° C., when compared to initial results. No significant changes were observed for the pH nor the particle size.

6.2. Testing at 25° C./60% RH

No changes were observed in appearance of the container and appearance of the content up to 3 months stored at 25° C., when compared to initial results. The initial pH 6.6 decreased to pH 6.3 for 3 month respectively. No significant changes observed for particle size by photon correlation spectroscopy and quantification of phospholipids up to 3 months. Subvisible particulate matter increased, however values remained in the acceptance range.

6.3. Testing at 40° C./75% RH

No changes were observed in appearance of container and appearance of the content up to 3 months stored at 40° C., when compared to initial results. Slight changes were observed for the pH, which slightly decreased from pH 6.6 initially, to 6.3 after 3 months storage at 40° C.

No significant changes were observed for particle size by photon correlation spectroscopy and quantification of phospholipids up to 3 months storage at 40° C. Significant differences were observed in the subvisible particulate matter testing. However, these conditions are considered as stress conditions when compared to the long term storage of 5° C.

6.4. Photostability

The photostability testing was performed with the product in a glass vial and compared with a vial protected from light in a carton box. In the photostability study, no significant changes were observed in parameters of appearance of the container, appearance of the content, pH of solution, visible particulate matter and quantification of phospholipids after storage.

Conclusions

Satisfactory stability data were demonstrated for long term conditions of 5° C. and accelerated conditions of 25° C./60% RH up to 3 months. Satisfactory stability data were shown for accelerated conditions at 40° C./75% RH up to 1.5 months, limited by the subvisible particles matters results. For appearance of the container, appearance of the content and particle size no changes were observed for all storage conditions up to 3 months. pH values were stable and in the specification range for all storage conditions. Satisfactory stability data were showed at long term condition of 5° C./ambient RH. The vehicle is considered to be photostable.

Example 7: In Vitro Release Assay, Compound A: The Release of Compound A from Small Liposomes to an Acceptor Comprising an Excess Lipids Present as Large Multilamellar Vesicles (MLVs)

The aim of this experiment was to investigate the release rate of Compound A from small unilamellar vesicles (SUV; used here as a drug carrier system, see Example 3A) to large multilamellar vesicles (MLVs) consisting of egg phospholipids, and used as a lipophilic acceptor for drug released (see Shabbits J. A., Chiu G. N. and Mayer L. D. "Development of an in vitro drug release assay that accurately predicts in vivo drug retention for liposome-based delivery systems" *Journal of Controlled Release* 2002, 84(3), 161-170).

Preparation and Performance of Release Study using Multilamellar Vesicles as Acceptor Preparation and Characterization of MLVs Multilamellar vesicles were prepared by using the Film-Hydration method. In short, egg phospholipids (Lipoid E 80 S) were weighed out and completely dissolved in organic solvent (EtOH/DCM at 4:1 v/v) to assure a homogenous mixture of all components.

Next, the organic solvent was removed using rotary evaporation (first step: 200 mbar, 50° C., 2 hours; second step: 30 mbar, 50° C., 45 minutes) to yield a homogenous lipid film. To assure complete removal of the organic solvent, the flask was flushed with nitrogen. Next, the film was rehydrated using phosphate buffered saline (PBS, pH 7.4) yielding MLVs and upon complete rehydration the MLVs were exposed to sonication for 15 minutes.

To have the MLVs resuspended in the same buffer system as the SUVs, the suspension was centrifuged for 10 minutes at 14,000 g, the supernatant (PBS) was removed, and replaced by sucrose histidine buffer. Lastly, the mixture was vortexed thoroughly to assure complete redispersion of the MLVs in the new medium before starting the release experiment.

MLV formulations were characterized based on their size by means of laser diffraction using a HELOS KR (SympaTec) system after a 1:5000 dilution using PBS giving $x_{10}$, $x_{50}$, and $x_{90}$ values.

$x_{10}$=particle dimension corresponding to 10% of the cumulative undersize distribution, $x_{50}$=medium particle dimension (i.e., 50% of the particles are smaller and 50% of the particles are larger), and $x_{90}$=particle dimension corresponding to 90% of the cumulative undersize distribution.

TABLE 7.1

Size distribution of MLVs

| Formulation | Size (μm) | | |
|---|---|---|---|
| | $x_{10}$ | $x_{50}$ | $x_{90}$ |
| PBS-loaded MLV (100% ePL) in PBS | 2.98 | 5.79 | 11.56 |

Release Study Using MLVs

Figure 3:
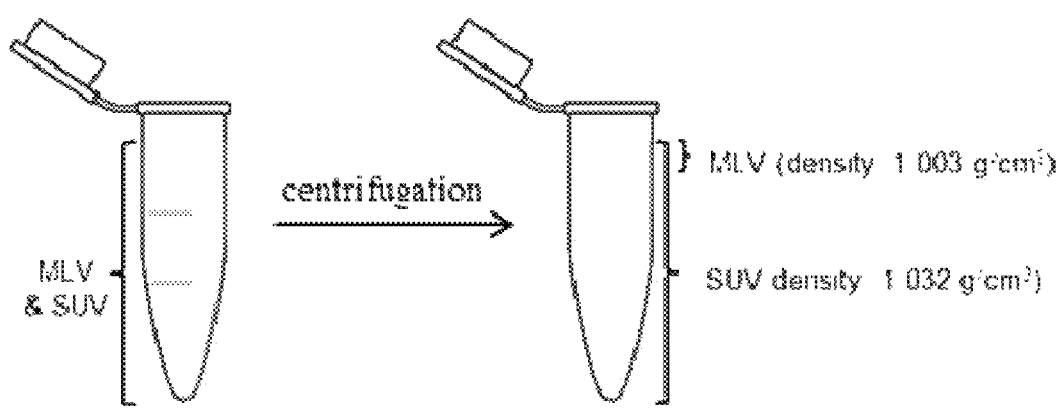
FIG. 3 shows is a schematic depicting the principle of the MLV-based release assay allowing to monitor the release of compound A from the liposomes to MLVs.

For the release study using MLVs the following setup was used for all experiments:

SUVs (donor) were mixed with MLVs (acceptor) in a 25 ml Erlenmeyer flask with a stopper under stirring (500 rpm) at various ratios (1:40, 1:100, 1:200, 1:500; SUV:MLV v/v). 1 ml samples were taken at different time points and immediately centrifuged (14'000 rpm, 10 minutes) to separate the MLVs from SUVs for further processing. FIG. 3 herein is a schematic depicting the principle of the MLV-based release assay.

Next, the MLV portion was removed via suction and 50 μl of the SUV portion were mixed with 450 μl of ACN:H$_2$O for HPLC sample preparation. The sample was then centrifuged (14'000 rpm, 10 minutes), the supernatant was filtered using a 0.22 μm filter and injected into the HPLC for analysis.

High Performance Liquid Chromatography Method for Compound A

A high performance liquid chromatography (HPLC) system with UV detection including the following equipment settings and solvent systems were employed:

| | |
|---|---|
| Instrument | Shimadzu LC2010C HT |
| Column | Waters Symmetry Shield, RP18, 3.5 μm, 3 × 150 mm |
| Column condition | 45° C. |
| Mobile phase | A) ACN:H$_2$O:FA:NH$_4$OH (20:80:1:0.4) |
| | B) ACN:H$_2$O:FA:NH$_4$OH (80:20:1:0.4) |
| Solvent gradient | Multi-Step Gradient |
| Solvent flow | 1.0 mL/min |
| Pressure | Maximum 270 bar |
| Automatic sample | Samples were injected using an autosampler |
| UV-detection | HPLC-UV detector set to 210 nm and 245 nm |

Solvent Gradient for HPLC

| Retention (min) | Flow (ml/min) | % A | % B |
|---|---|---|---|
| 0 | 1 | 40 | 60 |
| 0 | 1 | 40 | 60 |
| 1 | 1 | 40 | 60 |
| 4 | 1 | 100 | 0 |
| 4.1 | 1 | 40 | 60 |
| 5 | 1 | 40 | 60 |

Compound A Release Assay Using MLV

Compound A release was measured using MLVs as the acceptor compartment. Here, Compound A-loaded SUVs (7.5 mg/ml) were added to these MLVs at different ratios (v/v). FIG. 4 shows the release profile of Compound A from SUV to 100% ePL at various different SUV:MLV ratios (v/v).

Note: For all MLV release experiments, the maximum concentration (maxC=100%) was obtained by diluting the 7.5 mg/ml loaded SUVs 1 to 40, 1 to 100, 1 to 200, or 1 to 500 (v/v) in Sucrose Histidine buffer instead of MLVs.

Using this type of experimental setup, a very fast release of Compound A from the SUV to the acceptor MLVs was observed. Here, for the 1 to 40 dilution only about 44% of the initial amount of Compound A applied was detectable in the SUV portion of the sample after only 2 minutes. Therefore, ~60% had been released or transferred to the acceptor MLV portion at this point already. Moreover, increasing the dilution factor (1:100, 1:200, 1:500 SUV:MLV v/v) only accelerated and increased drug release, as at t=2 minutes the 1 to 100 dilution demonstrated a release of ~70%, the 1 to 200 dilution ~80%, and for the 1 to 500 dilution almost 90% of the total amount of drug were not detectable anymore in the SUVs at t=2 minutes and were therefore released to the acceptor compartment.

Conclusion

A fast release profile of Compound A was demonstrated with up to 90% of drug substance being released after only 2 minutes. The data show that the liposomes do not physically retain Compound A encapsulated in the presence of excess lipid, but that there is a fast redistribution of Compound A over all lipids present during the incubation. In vivo a comparable behavior is expected. The formulation provides a particularly favourable balance of effective solubilisation of Compound A, with a desirable fast release profile of Compound A.

Example 8: Organic Concentrate Composition Comprising Compound A and PEG300, Variant 1

| Composition | Composition per mL [mg] | Excipient function |
|---|---|---|
| Compound A | 60 | |
| DMPG-Na (1,2-Dimyristoyl-sn-glycero-3-phospho-rac-glycerol, sodium salt) | 4 | stabiliser |
| Ethanol | 94 | solvent |
| PEG300 | 224 | solvent, stabiliser |
| propylene glycol | 728 | solvent |

The composition can be made using a similar method to Example 1, or using methods well known to the skilled person.

Example 9: Organic Concentrate Composition Comprising Compound A and PEG300, Variant 2

| Composition | Composition per mL [mg] | Excipient function |
|---|---|---|
| Compound A | 60 | |
| DMPG-Na (1,2-Dimyristoyl-sn-glycero-3-phospho-rac-glycerol, sodium salt) | 4 | stabiliser |
| Ethanol | 79 | solvent |
| PEG300 | 224 | solvent, stabilizer |
| propylene glycol | 792 | solvent |

The composition can be made using a similar method to Example 1, or using methods well known to the skilled person.

Example 10: Organic Concentrate Composition Comprising Compound A and PEG300, Variant 3

| Composition | Composition per mL [mg] | Excipient function |
|---|---|---|
| Compound A | 60 | |
| DMPG-Na (1,2-Dimyristoyl-sn-glycero-3-phospho-rac-glycerol, sodium salt) | 2 | stabiliser |
| Ethanol | 94 | solvent |
| PEG300 | 224 | solvent, stabilizer |
| propylene glycol | 851 | solvent |

The composition can be made using a similar method to Example 1, or using methods well known to the skilled person.

Reference Example 11: Organic Concentrate Comprising Compound A, without Stabiliser Against Jellification

| Composition | Composition per mL [mg] | Excipient function |
|---|---|---|
| Compound A | 60 | |
| DMPG-Na (1,2-Dimyristoyl-sn-glycero-3-phospho-rac-glycerol, sodium salt) | 4 | stabiliser |
| Ethanol | 94 | solvent |
| propylene glycol | 851 | solvent |

The composition can be made using a similar method to Example 1, or using methods well known to the skilled person.

Example 12: Physical Stability Examination of the Organic Concentrates of Examples 1, 8 to 10

Physical stability examination was evaluated using two separate methods: a) resistance to the seeding and b) exploratory stability under continuous stirring at 250 rpm at 2° C.

a. A seeding experiment was performed by adding ~1 µL of a jellified formulation (Compound A: 60 mg/ml, DMPG: 4.0 mg/ml, propylene glycol 851 mg/ml, ethanol: 94 mg/ml: this solution jellified when stored under stirring at 2° C.) into the clear concentrates of Examples 1, 8 and 9. The samples were vortexed for 10 seconds and stored in the fridge overnight at 2-8° C. Examples 1, 8 and 9 did not reveal jellification of Compound A upon seeding.

b. Exploratory stability experiments under continuous stirring were performed by placing 2 ml of each organic concentrate into a glass tube, and stirring homogenously at 250 rpm at 2° C. As shown in the Table below, jellification did not occur for formulations described in Examples 1, 8 to 10, during 10 days. After 13 days the composition of Example 1 had jellified, yet formulations described in Examples 8 to 10 remained stable, i.e. clear solutions.

| | Example 1 | Example 8 | Example 9 | Example 10 | Reference Example 11 |
|---|---|---|---|---|---|
| 48 hours | Clear solution | Clear solution | Clear solution | Clear solution | Non-reversible white gel |
| 1 week | Clear solution | Clear solution | Clear solution | Clear solution | Non-reversible white gel |
| 10 days | Clear solution | Clear solution | Clear solution | Clear solution | — |
| 13 days | Reversible white gel | Clear solution | Clear solution | Clear solution | — |

Advantageously, the formulations comprising PEG300 resisted jellification in the stirring experiment described above along with resistance to the seeding. Jellification of Example 1 can be managed by selecting an appropriate storage temperature, for example by storage at room temperature.

Example 13: Liposomal Loading Using the Concentrate Compositions of Examples 1, 8 to 10

Loading of liposomes was tested at a 23.7 mL scale, using the same approach as described in Example 3A.

The organic concentrate of Examples 8 to 10 exhibited comparable liposome-loading characteristics to Example 1. Examples 8 to 10 resulted in liposomal formulations with comparable turbidity to those resulting from Example 1.

| | Liposomal formulation from Example 1 concentrate | Liposomal formulation from Example 8 concentrate | Liposomal formulation from Example 9 concentrate | Liposomal formulation from Example 10 concentrate |
|---|---|---|---|---|
| Size, nm | 54.3 | 58.3 | 54 | 62.6 |
| PDI | 0.287 | 0.298 | 0.283 | 0.282 |
| Transmittance, % | 71.2 | 72.9 | 72.2 | 70.7 |

Size, nm, calculated as described herein;
PDI: Polydispersity index

In order to facilitate Example 8 and Example 9 liposomal loading, loading with 19 G needles was examined and compared with a 21 G needle. Use of 19 G needle resulted in slightly smaller size particles and slightly lower turbidity compared to the injection with 21 G needle.

Example 14: Physical Stability of Placebo Organic Concentrate Formulations

Placebo formulations (without Compound A) were tested at −20° C.; an extreme condition that may accelerate possible precipitation of the formulation components. Physical stability of the placebo organic concentrates described below was examined up to 17 days.

| | Placebo of Example 1 | Placebo of Example 8 | Placebo of Example 10 |
|---|---|---|---|
| Composition mg/ml | | | |
| Propylene glycol | 851 | 728 | 728 |
| Ethanol | 94 | 94 | 94 |
| DMPG-Na (1,2-Dimyristoyl-sn-glycero-3-phospho-rac-glycerol, sodium salt) | 4 | 4 | 2 |

-continued

|  | Placebo of Example 1 | Placebo of Example 8 | Placebo of Example 10 |
|---|---|---|---|
| PEG300 | 0 | 224 | 224 |
| NaCl | 4 | 0 | 0 |
| Water | 10 | 0 | 0 |
| Observations |  |  |  |
| 48 hours | turbid | clear | clear |
| 6 days | precipitation | clear | clear |
| 10 days | precipitation | clear | clear |
| 17 Days | precipitation | clear | clear |

Precipitation was observed in the placebo composition of Example 1. The placebo composition of Examples 8 and 10 remained clear and no precipitation was observed during the experiment.

Example 15: Chemical Stability of the Active Organic Concentrates of Examples 1, 8 and 9

The chemical stability of active compound within the formulations of Examples 1, 8 and 9 was tested, in particular with an aim to investigate levels of impurities resulting from oxidative degradation, and the formation of the undesirable atropisomer.

Identity, Assay and Degradation Products by HPLC

| Principle | RP HPLC method with ion pairing and UV detection |
|---|---|
| Reagents |  |
| Acetonitrile | gradient grade, e.g. Merck LiChrosolv No. 100030 |
| Ethanol | LC grade, e.g. Merck 1.00983 |
| Formic acid | LC grade, e.g. Prolabo No. 84865.260 |
| Ammonium hydroxide 25% | Analytical grade, e.g. Sigma No. 09860 |
| $H_2O_2$ 30% | Analytical grade, e.g. Sigma No. 95313 |
| Water | MilliQ or HPLC grade |
| Diluted ammonium hydroxide | In a 50.0 mL volumetric flask, introduce 2.5 mL of ammonium hydroxide 25% and complete to volume with purified water. |
| Diluent | Ethanol |
| Materials |  |
| Glassware | Amber glassware shall be used |
| Equipment |  |
| Apparatus | HPLC system with gradient elution and UV detector, e.g. Agilent 1290 with UV detector or equivalent |
| Column | Acquity BEH C18 Length: 100 mm, internal diameter: 2.1 mm Particle size: 1.7 μm |
| Additional equipment | Ultrasonic bath, analytical balance, microbalance |
| Chromatographic conditions |  |
| Separation mode | Gradient |
| Mobile Phase A | Water + acetonitrile + formic acid, 95 + 5 + 0.02 (v/v/v) aqueous fraction pH = 4.9, adjusted with ammonium hydroxide. Add 200 μL of formic acid to 950 mL of water. Adjust pH to 4.9 using diluted ammonium hydroxide. Add 50 mL of acetonitrile. |
| Mobile Phase B | Water + acetonitrile + formic acid, 5 + 95 + 0.02 (v/v/v), aqueous fraction pH = 4.9, adjusted with ammonium hydroxide. Add 200 μL of formic acid to 50 mL of water. Adjust pH to 4.9 using diluted ammonium hydroxide. Add 950 mL of acetonitrile. Different volumes may be used as long as the volume ratio remains the same. |

Gradient table

| Time [min] | Phase A [%] | Phase B [%] |
|---|---|---|
| 0.0 | 100 | 0 |
| 2.0 | 100 | 0 |
| 3.0 | 60 | 40 |
| 11.0 | 52 | 48 |
| 14.0 | 10 | 90 |
| 14.3 | 100 | 0 |
| 16.0 | 100 | 0 |

| Flow rate | 0.6 mL/min |
|---|---|
| Detection | UV 210 nm |
| Column Temperature | 40° C. |
| Autosampler Temperature | 2-8° C. |
| Injection wash solvent | Ethanol using flush port with minimum 10 seconds |
| Injection volume | 5 μl of the test and reference solutions, equivalent to about 1.0 μg of drug substance name in the reference solution |

| Composition | Time point (weeks) | Temp ° C. | Undesirable Atropoisomer, % | Ox1 % | Ox2 % | SUM DPs |
|---|---|---|---|---|---|---|
| Example 8 | 6 | 5 | <0.1 | <0.1 | <0.1 (0.06*) | <0.1 |
|  |  | 40 | 3.78 | <0.1 (0.04*) | 0.13 | 0.13 |
| Example 8 | 8 | 5 | <0.1 | <0.1 | <0.1 (0.05*) | <0.1 |
|  |  | 40 | 4.86 | <0.1 | 0.18 | 0.28 |
| Example 9 | 6 | 5 | <0.1 | <0.1 | <0.1 (0.07*) | <0.1 |
|  |  | 40 | 3.53 | <0.1 (0.02*) | 0.11 | 0.11 |
| Example 9 | 8 | 5 | <0.1 | <0.1 | <0.1 (0.04*) | <0.1 |
|  |  | 40 | 4.42 | <0.1 | 0.14 | 0.14 |
| Example 1 | 6 | 5 | 1.54 | <0.1 | <0.1 (0.05*) | <0.1 |
|  |  | 40 | 4.63 | <0.1 | <0.1 (0.04*) | <0.1 |
| Example 1 | 8 | 5 | 1.62 | <0.1 | <0.1 (0.04*) | <0.1 |
|  |  | 40 | 6.06 | <0.1 | <0.1 (0.05*) | <0.1 |
| Example 1, freshly prepared | 5 | 5 | <0.1 | <0.1 | <0.1 (0.04*) | <0.1 |
|  |  | 40 | 2.82 | <0.1 | <0.1 (0.06*) | <0.1 |
| Example 1, freshly prepared | 7 | 5 | <0.1 | <0.1 | <0.1 (0.03*) | <0.1 |
|  |  | 40 | 3.58 | <0.1 | <0.1 (0.05*) | <0.1 |

*Below reporting level; % are expressed as peak area %; Ox1 and Ox2 are two oxidative degradation products. Sum DP's is the sum of the degradation products, with the exception of the atropoisomers, above the reporting level. 'Example 1' composition was prepared 8 months before the study, stored at 25° C. up to the start of the study. 'Example 1, freshly prepared' composition was prepared just before the start of the study and immediately placed at 5° C. and 40° C., respectively.

Oxidative degradation products were low across all the formulation variants above. The increase of undesirable atropisomer detected was temperature and time related, but was not altered by the formulation variants tested.

A visual check revealed no change of concentrate colour in any of the formulations tested above.

The invention claimed is:
1. An organic concentrate composition comprising:
(a) Compound A which is 2-{[5-{3-chloro-2-methyl-4-[2-(4-methylpiperazin-1-yl)ethoxy]phenyl}-6-(4-fluoro- phenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof, (b) a negatively charged or polar phospholipid stabiliser, and (c) a stabiliser against jellification.

2. The organic concentrate composition according to claim 1, wherein Compound A is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof.

3. The organic concentrate composition according to claim 1, wherein Compound A is the free molecule.

4. The organic concentrate composition according to claim 1, wherein the negatively charged or polar phospholipid stabiliser is selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3[Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, egg lecithin, soy lecithin, and sodium oleate.

5. The organic concentrate composition according to claim 4, wherein the negatively charged or polar phospholipid stabiliser is 1,2-Dimyristoyl-sn-glycero-3-phospho-rac-glycerol, sodium or ammonium salt, egg lecithin, or soy lecithin.

6. The organic concentrate composition according to claim 1, wherein the stabiliser against jellification is a polymer or an electrolyte.

7. The organic concentrate composition according to claim 1, wherein the stabiliser against jellification is an electrolyte selected from sodium chloride, potassium chloride, sodium phosphate di- and monobasic, ammonium sulphate and arginine.

8. The organic concentrate composition according to claim 1, wherein the stabiliser against jellification is sodium chloride.

9. The organic concentrate composition according to claim 1, wherein the stabiliser against jellification is a polymer selected from PEG300 and PEG400.

10. The organic concentrate composition according to claim 1, further comprising a solvent.

11. The organic concentrate composition according to claim 10, wherein the solvent is selected from propylene glycol, ethanol, and/or mixtures thereof.

12. A pharmaceutical composition comprising a mixture of the organic concentrate composition according to claim 1 and a liposomal vehicle, wherein the liposomal vehicle comprises a phospholipid and a tonicity adjusting agent.

13. The pharmaceutical composition according to claim 12, wherein the phospholipid is selected from egg lecithin, soy lecithin, and synthetic phospholipids.

14. The pharmaceutical composition according to claim 12, wherein the phospholipid is of the formula

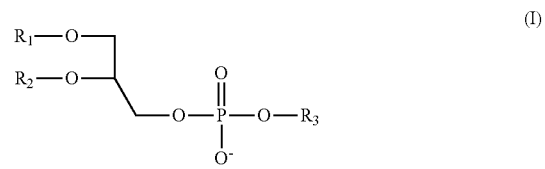

(I)

wherein
R$_1$ represents C$_{10}$-C$_{24}$acyl;
R$_2$ represents C$_{10}$-C$_{24}$acyl;
R$_3$ represents hydrogen, 2-trimethylamino-1-ethyl, 2-amino-1-ethyl, C$_1$-C$_4$alkyl, C$_1$-C$_5$alkyl substituted by carboxy, C$_2$-C$_5$alkyl substituted by carboxy and hydroxy, C$_2$-C$_5$alkyl substituted by carboxy and amino, an inositol group or a glyceryl group;
or a salt of such compound.

15. The pharmaceutical composition according to claim 12, wherein the phospholipid is selected from egg lecithin, soy lecithin, POPC (palmitoyl oleoyl phosphatidylcholine), DOPC (1,2-Dioleoyl-sn-glycero-3-phosphocholine), and DMPC (1,2-Dimyristoyl-sn-glycero-3-phosphocholine).

16. The pharmaceutical composition according to claim 12, wherein the phospholipid is egg lecithin or soy lecithin comprising at least 70% phosphatidylcholine.

17. The pharmaceutical composition according to claim 12, wherein the tonicity adjusting agent is selected from dextrose, glucose, mannitol, sucrose, lactose, trehalose, glycerine and NaCl.

18. A liposomal pharmaceutical composition comprising, in addition to liposomes:

(a) Compound A which is 2-{[5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof; and (b) a stabiliser against jellification.

19. The liposomal pharmaceutical composition according to claim 18, comprising:

(a) Compound A which is (2R)-2-{[5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof, and (b) a stabiliser against jellification, which is a polymer or an electrolyte.

20. The liposomal pharmaceutical composition according to claim 19, wherein Compound A is the free molecule.

21. The liposomal pharmaceutical composition according to claim 19, wherein the stabiliser against jellification is an electrolyte selected from sodium chloride, potassium chloride, sodium phosphate di- and monobasic, ammonium sulphate and arginine.

22. The liposomal pharmaceutical composition according to claim 19, wherein the stabiliser against jellification is sodium chloride.

23. The liposomal pharmaceutical composition according to claim 19, wherein the stabiliser against jellification is a polymer selected from PEG300 and PEG400.

24. The liposomal pharmaceutical composition according to claim 18, further comprising a negatively charged or polar phospholipid stabiliser.

25. The liposomal pharmaceutical composition according to claim 24, wherein the negatively charged or polar phospholipid stabiliser is selected from DMPG sodium or ammonium salt (1,2-Dimyristoyl-sn-glycero-3-phospho-rac-glycerol, or dimyristoyl phosphatidylglycerol), POPG sodium salt (1-Palmitoyl-2-oleoyl-sn-glycero-3[Phospho-rac-(1-glycerol)]), DOPS sodium salt (1,2-Dioleoyl-sn-glycero-3-phosphoserine), DOPG sodium salt (1,2-Dioleoyl-sn-glycero-3 [Phospho-rac-(1-glycerol)]), DPPG (1,2-Dipalmitoyl-sn-glycero-3[Phospho-rac-(1-glycerol)]) sodium or ammonium salt, DSPG (1,2-Distearoyl-sn-glycero-3[Phospho-rac-(1-glycerol)]) sodium or ammonium salt, soy phosphatidic acid (PA) sodium salt, egg phosphatidic acid (PA) sodium salt, soy phosphatidylserine (PS) sodium salt, egg phosphatidylglycerol (PG) sodium salt, soy phosphatidylglycerol (PG) sodium salt, phosphatidyl inositol (PI) sodium salt, egg lecithin, soy lecithin, and sodium oleate.

26. The liposomal pharmaceutical composition according to claim 24, wherein the negatively charged or polar phospholipid stabiliser is selected from 1,2-Dimyristoyl-sn-glycero-3-phospho-rac-glycerol, sodium or ammonium salt, egg lecithin, and soy lecithin.

27. The liposomal pharmaceutical composition according to claim 18, further comprising a solvent.

28. The liposomal pharmaceutical composition according to claim 27, wherein the solvent is selected from propylene glycol, ethanol, and/or mixtures thereof.

29. The liposomal pharmaceutical composition according to claim 18, wherein the liposome comprises a phospholipid selected from egg lecithin, soy lecithin, and synthetic phospholipids.

30. The liposomal pharmaceutical composition according to claim 29, wherein the phospholipid is of the formula

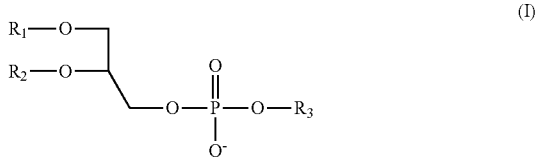

(I)

wherein
R$_1$ represents C$_{10}$-C$_{24}$acyl;
R$_2$ represents C$_{10}$-C$_{24}$acyl;
R$_3$ represents hydrogen, 2-trimethylamino-1-ethyl, 2-amino-1-ethyl, C$_1$-C$_4$alkyl, C$_1$-C$_5$alkyl substituted by carboxy, C$_2$-C$_5$alkyl substituted by carboxy and hydroxy, C$_2$-C$_5$alkyl substituted by carboxy and amino, an inositol group or a glyceryl group;
or a salt of such compound.

31. The liposomal pharmaceutical composition according to claim 29, wherein the phospholipid is selected from egg lecithin, soy lecithin, POPC (palmitoyl oleoyl phosphatidylcholine), DOPC (1,2-Dioleoyl-sn-glycero-3-phosphocholine), and DMPC (1,2-Dimyristoyl-sn-glycero-3-phosphocholine).

32. The liposomal pharmaceutical composition according to claim 29, wherein the phospholipid is egg lecithin or soy lecithin comprising at least 70% phosphatidylcholine.

33. The liposomal pharmaceutical composition according to claim 18, further comprising a tonicity adjusting agent.

34. The liposomal pharmaceutical composition according to claim 33, wherein the tonicity adjusting agent is selected from dextrose, glucose, mannitol, sucrose, lactose, trehalose, glycerine and NaCl.

35. A method of treating cancer in a subject in need thereof, comprising administration of an effective amount of the organic concentrate composition according to claim 1.

36. A method of treating cancer in a subject in need thereof, comprising administration of an effective amount of the pharmaceutical composition according to claim 12.

37. A method of treating cancer in a subject in need thereof, comprising administration of an effective amount of the pharmaceutical composition according to claim 18.

38. A combination comprising
(a) the pharmaceutical composition according to claim 12, and
(b) one or more therapeutically active agents, for simultaneous, sequential or separate use.

39. A combination comprising:
(a) the pharmaceutical composition according to claim 18, and
(b) one or more therapeutically active agents, for simultaneous, sequential or separate use.

40. A kit comprising:
(a) a liposomal vehicle and
(b) the organic concentrate composition according to claim 1.

41. The method according to claim 36, wherein the cancer is selected from cancers of the bladder, brain, breast and uterus, chronic lymphoid leukaemias, cancer of the colon, œsophagus and liver, lymphoblastic leukaemias, acute myeloid leukaemia, lymphomas, non-Hodgkin's B-cell lymphoma, diffuse large B-cell lymphoma, melanomas, malignant haemopathies, myelodysplastic syndrome, myelomas, multiple myeloma, ovarian cancer, non-small-cell lung cancer, prostate cancer, pancreatic cancer and small-cell lung cancer.

42. The method according to claim 37, wherein the cancer is selected from cancers of the bladder, brain, breast and uterus, chronic lymphoid leukaemias, cancer of the colon, œsophagus and liver, lymphoblastic leukaemias, acute myeloid leukaemia, lymphomas, non-Hodgkin's B-cell lymphoma, diffuse large B-cell lymphoma, melanomas, malignant haemopathies, myelodysplastic syndrome, myelomas, multiple myeloma, ovarian cancer, non-small-cell lung cancer, prostate cancer, pancreatic cancer and small-cell lung cancer.

* * * * *

UNITED STATES PATENT AND TRADEMARK OFFICE
CERTIFICATE OF CORRECTION

PATENT NO. : 10,722,466 B2
APPLICATION NO. : 16/344431
DATED : July 28, 2020
INVENTOR(S) : Wessels et al.

Page 1 of 1

It is certified that error appears in the above-identified patent and that said Letters Patent is hereby corrected as shown below:

In the Claims

Column 36, Line 38: "œsophagus" should read -- œsophagus --.

Signed and Sealed this
Tenth Day of November, 2020

Andrei Iancu
*Director of the United States Patent and Trademark Office*